US012788628B2

(12) United States Patent
Vidlund et al.

(10) Patent No.: US 12,788,628 B2
(45) Date of Patent: Nov. 10, 2026

(54) TREATING EYE DISEASES BY DEPLOYING A STENT

(71) Applicant: J.D. Franco & Co., LLC, Plano, TX (US)

(72) Inventors: Robert Vidlund, Forest Lake, MN (US); Michael Calhoun, Lighthouse Point, FL (US); Jeff Franco, Plano, TX (US)

(73) Assignee: J.D. FRANCO & CO., LLC, Plano, TX (US)

( * ) Notice: Subject to any disclaimer, the term of this patent is extended or adjusted under 35 U.S.C. 154(b) by 60 days.

(21) Appl. No.: 18/328,074

(22) Filed: Jun. 2, 2023

(65) Prior Publication Data

US 2024/0099882 A1 Mar. 28, 2024

Related U.S. Application Data

(63) Continuation of application No. 16/997,513, filed on Aug. 19, 2020, now Pat. No. 11,701,255, which is a
(Continued)

(51) Int. Cl.
*A61F 9/007* (2006.01)
*A61F 2/06* (2013.01)
(Continued)

(52) U.S. Cl.
CPC ................ *A61F 9/007* (2013.01); *A61F 2/06* (2013.01); *A61F 2/856* (2013.01);
(Continued)

(58) Field of Classification Search
CPC .... A61F 2/856; A61F 2/06; A61F 2/14; A61F 2002/061; A61F 2002/065; A61F 2002/068; A61F 2002/821; A61F 9/007
See application file for complete search history.

(56) References Cited

U.S. PATENT DOCUMENTS

| | | | |
|---|---|---|---|
| 2,690,595 | A | 10/1954 | Raiche |
| 3,367,101 | A | 2/1968 | Garnet et al. |

(Continued)

FOREIGN PATENT DOCUMENTS

| | | | |
|---|---|---|---|
| EP | 2 495 006 | A1 | 9/2012 |
| WO | WO 98/52639 | A1 | 11/1998 |

(Continued)

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.

(Continued)

*Primary Examiner* — William H Matthews
(74) *Attorney, Agent, or Firm* — Bookoff McAndrews, PLLC

(57) ABSTRACT

A method of treating an eye of a patient may include positioning an expandable strut structure within at least one of an internal carotid artery, an ophthalmic artery, or an ostium at a junction between the internal carotid artery and the ophthalmic artery. Additionally, the method may include directing blood flow towards the ophthalmic artery via a diverter element associated with the expandable strut structure.

18 Claims, 15 Drawing Sheets

Related U.S. Application Data continuation of application No. 16/151,741, filed on Oct. 4, 2018, now Pat. No. 10,779,929.

(60) Provisional application No. 62/568,862, filed on Oct. 6, 2017.

(51) Int. Cl.

| | |
|---|---|
| ***A61F 2/14*** | (2006.01) |
| ***A61F 2/856*** | (2013.01) |
| *A61F 2/82* | (2013.01) |
| *A61F 2/915* | (2013.01) |

(52) U.S. Cl.

CPC .......... *A61F 2002/068* (2013.01); *A61F 2/14* (2013.01); *A61F 2002/821* (2013.01); *A61F 2/915* (2013.01); *A61F 2210/0014* (2013.01); *A61F 2230/0067* (2013.01)

(56) References Cited

U.S. PATENT DOCUMENTS

| | | | |
|---|---|---|---|
| 3,435,826 | A | 4/1969 | Fogarty |
| 3,970,090 | A | 7/1976 | Loiacono |
| 4,224,929 | A | 9/1980 | Furihata |
| 4,403,612 | A | 9/1983 | Fogarty |
| 4,445,897 | A | 5/1984 | Ekbladh et al. |
| 4,794,931 | A | 1/1989 | Yock |
| 4,857,045 | A | 8/1989 | Rydell |
| 4,886,061 | A | 12/1989 | Fischell et al. |
| 4,894,051 | A | 1/1990 | Shiber |
| 4,898,575 | A | 2/1990 | Fischell et al. |
| 4,926,858 | A | 5/1990 | Gifford, III et al. |
| 4,936,835 | A | 6/1990 | Haaga |
| 4,950,277 | A | 8/1990 | Farr |
| 4,957,482 | A | 9/1990 | Shiber |
| 4,979,939 | A | 12/1990 | Shiber |
| 4,986,807 | A | 1/1991 | Farr |
| 5,000,185 | A | 3/1991 | Yock |
| 5,000,734 | A | 3/1991 | Boussignac et al. |
| 5,007,896 | A | 4/1991 | Shiber |
| 5,019,088 | A | 5/1991 | Farr |
| 5,024,651 | A | 6/1991 | Shiber |
| 5,026,384 | A | 6/1991 | Farr et al. |
| 5,087,265 | A | 2/1992 | Summers |
| 5,100,425 | A | 3/1992 | Fischell et al. |
| 5,135,531 | A | 8/1992 | Shiber |
| 5,176,693 | A | 1/1993 | Pannek, Jr. |
| 5,292,332 | A | 3/1994 | Lee |
| 5,313,949 | A | 5/1994 | Yock |
| 5,314,438 | A | 5/1994 | Shturman |
| 5,318,576 | A | 6/1994 | Plassche et al. |
| 5,336,234 | A | 8/1994 | Vigil et al. |
| 5,366,464 | A | 11/1994 | Belknap |
| 5,395,311 | A | 3/1995 | Andrews |
| 5,402,790 | A | 4/1995 | Jang et al. |
| 5,409,454 | A | 4/1995 | Fischell et al. |
| 5,415,634 | A | 5/1995 | Glynn et al. |
| 5,419,761 | A | 5/1995 | Narayanan et al. |
| 5,507,292 | A | 4/1996 | Jang et al. |
| 5,554,119 | A | 9/1996 | Harrison et al. |
| 5,709,701 | A | 1/1998 | Parodi |
| 5,820,595 | A | 10/1998 | Parodi |
| 5,897,567 | A | 4/1999 | Ressemann et al. |
| 5,951,514 | A | 9/1999 | Sahota |
| 5,972,019 | A | 10/1999 | Engelson et al. |
| 6,010,522 | A | 1/2000 | Barbut et al. |
| 6,146,370 | A | 11/2000 | Barbut |
| 6,206,868 | B1 | 3/2001 | Parodi |
| 6,302,908 | B1 | 10/2001 | Parodi |
| 6,336,933 | B1 | 1/2002 | Parodi |
| 6,344,054 | B1 | 2/2002 | Parodi |
| 6,413,235 | B1 | 7/2002 | Parodi |
| 6,423,032 | B2 | 7/2002 | Parodi |
| 6,494,890 | B1 | 12/2002 | Shturman et al. |
| 6,540,712 | B1 | 4/2003 | Parodi et al. |
| 6,595,980 | B1 | 7/2003 | Barbut |
| 6,623,471 | B1 | 9/2003 | Barbut |
| 6,626,861 | B1 | 9/2003 | Hart et al. |
| 6,641,573 | B1 | 11/2003 | Parodi |
| 6,645,222 | B1 | 11/2003 | Parodi et al. |
| 6,824,558 | B2 | 11/2004 | Parodi |
| 6,827,726 | B2 | 12/2004 | Parodi |
| 6,837,881 | B1 | 1/2005 | Barbut |
| 6,855,162 | B2 | 2/2005 | Parodi |
| 6,902,540 | B2 | 6/2005 | Dorros et al. |
| 6,905,490 | B2 | 6/2005 | Parodi |
| 6,908,474 | B2 | 6/2005 | Hogendijk et al. |
| 6,929,634 | B2 | 8/2005 | Dorros et al. |
| 6,936,053 | B1 | 8/2005 | Weiss |
| 6,936,060 | B2 | 8/2005 | Hogendijk et al. |
| 6,974,469 | B2 | 12/2005 | Broome et al. |
| 7,195,611 | B1 | 3/2007 | Simpson et al. |
| 7,214,201 | B2 | 5/2007 | Burmeister et al. |
| 7,235,095 | B2 | 6/2007 | Haverkost et al. |
| 7,309,334 | B2 | 12/2007 | Von Hoffmann |
| 7,384,411 | B1 | 6/2008 | Condado |
| 7,604,612 | B2 | 10/2009 | Ressemann et al. |
| 7,806,906 | B2 | 10/2010 | Don Michael |
| 7,867,273 | B2 | 1/2011 | Pappas et al. |
| 7,901,445 | B2 | 3/2011 | Wallace et al. |
| 7,927,347 | B2 | 4/2011 | Hogendijk et al. |
| 8,123,779 | B2 | 2/2012 | Demond et al. |
| 8,157,760 | B2 | 4/2012 | Criado et al. |
| 8,267,956 | B2 | 9/2012 | Salahieh et al. |
| 8,353,850 | B2 | 1/2013 | Ressemann et al. |
| 8,409,237 | B2 | 4/2013 | Galdonik et al. |
| 8,414,516 | B2 | 4/2013 | Chang |
| 8,439,937 | B2 | 5/2013 | Montague et al. |
| 8,545,432 | B2 | 10/2013 | Renati et al. |
| 8,834,404 | B2 | 9/2014 | Beaudin |
| 8,852,226 | B2 | 10/2014 | Gilson et al. |
| 8,863,631 | B1 | 10/2014 | Janardhan et al. |
| 9,078,682 | B2 | 7/2015 | Lenker et al. |
| 9,241,699 | B1 | 1/2016 | Kume et al. |
| 9,259,215 | B2 | 2/2016 | Chou et al. |
| 9,265,512 | B2 | 2/2016 | Garrison et al. |
| 9,987,164 | B2 | 6/2018 | Calhoun |
| 10,195,077 | B2 | 2/2019 | Calhoun et al. |
| 10,265,085 | B2 | 4/2019 | Zaidat |
| 10,342,699 | B2 | 7/2019 | Calhoun et al. |
| 2001/0001114 | A1 | 5/2001 | Tsugita et al. |
| 2002/0038103 | A1 | 3/2002 | Estrada et al. |
| 2002/0077656 | A1 | 6/2002 | Ginn et al. |
| 2002/0077658 | A1 | 6/2002 | Ginn |
| 2002/0087128 | A1 | 7/2002 | Paques et al. |
| 2002/0143291 | A1 | 10/2002 | Slater |
| 2002/0151922 | A1 | 10/2002 | Hogendijk et al. |
| 2002/0165573 | A1 | 11/2002 | Barbut |
| 2003/0023200 | A1 | 1/2003 | Barbut et al. |
| 2003/0023227 | A1 | 1/2003 | Zadno-Azizi et al. |
| 2003/0199802 | A1 | 10/2003 | Barbut |
| 2003/0199819 | A1 | 10/2003 | Beck |
| 2003/0203958 | A1 | 10/2003 | Kunz et al. |
| 2005/0149117 | A1 | 7/2005 | Khosravi et al. |
| 2006/0089618 | A1 | 4/2006 | McFerran et al. |
| 2006/0136022 | A1 | 6/2006 | Wong, Jr. et al. |
| 2006/0173528 | A1 | 8/2006 | Feld et al. |
| 2006/0259132 | A1 | 11/2006 | Schaffer et al. |
| 2006/0276838 | A1 | 12/2006 | Wensel et al. |
| 2007/0026035 | A1 | 2/2007 | Burke et al. |
| 2008/0027519 | A1 | 1/2008 | Guerrero |
| 2008/0243229 | A1 | 10/2008 | Wallace et al. |
| 2009/0018455 | A1 | 1/2009 | Chang |
| 2009/0024072 | A1 | 1/2009 | Criado et al. |
| 2009/0030323 | A1 | 1/2009 | Fawzi et al. |
| 2009/0221961 | A1 | 9/2009 | Tal et al. |
| 2010/0076365 | A1 | 3/2010 | Riina et al. |
| 2010/0100045 | A1 | 4/2010 | Pravongviengkham et al. |
| 2010/0125244 | A1 | 5/2010 | McAndrew |
| 2010/0234884 | A1 | 9/2010 | Lafontaine et al. |
| 2011/0143993 | A1 | 6/2011 | Langer et al. |
| 2011/0152683 | A1 | 6/2011 | Gerrans et al. |
| 2011/0152998 | A1 | 6/2011 | Berez et al. |

(56) References Cited

U.S. PATENT DOCUMENTS

| | | | |
|---|---|---|---|
| 2011/0160762 | A1 | 6/2011 | Hogendijk et al. |
| 2011/0274748 | A1 | 11/2011 | Robinson et al. |
| 2012/0046679 | A1 | 2/2012 | Patel et al. |
| 2012/0078287 | A1 | 3/2012 | Barbut |
| 2012/0101510 | A1 | 4/2012 | Lenker et al. |
| 2013/0035628 | A1 | 2/2013 | Garrison et al. |
| 2013/0197621 | A1 | 8/2013 | Ryan et al. |
| 2013/0281788 | A1 | 10/2013 | Garrison |
| 2014/0154246 | A1 | 6/2014 | Robinson et al. |
| 2014/0222066 | A1 | 8/2014 | Tegels |
| 2015/0025562 | A1 | 1/2015 | Dinh et al. |
| 2015/0032121 | A1 | 1/2015 | Janardhan et al. |
| 2015/0065804 | A1 | 3/2015 | Kleyman |
| 2015/0231378 | A1 | 8/2015 | Pepper |
| 2015/0272732 | A1 | 10/2015 | Tilson et al. |
| 2015/0313607 | A1 | 11/2015 | Zhadkevich |
| 2015/0359547 | A1 | 12/2015 | Vale et al. |
| 2015/0359549 | A1 | 12/2015 | Lenker et al. |
| 2015/0366580 | A1 | 12/2015 | Lenihan et al. |
| 2016/0166754 | A1 | 6/2016 | Kassab et al. |
| 2016/0213893 | A1 | 7/2016 | Franklin |
| 2016/0279385 | A1 | 9/2016 | Katsurada et al. |
| 2016/0317328 | A1 | 11/2016 | Berez et al. |
| 2017/0164963 | A1 | 6/2017 | Goyal |
| 2017/0239453 | A1 | 8/2017 | Kawakita et al. |
| 2017/0274179 | A1 | 9/2017 | Sullivan et al. |
| 2017/0326001 | A1 | 11/2017 | Franco et al. |
| 2017/0348120 | A1 | 12/2017 | Calhoun et al. |
| 2018/0132876 | A1 | 5/2018 | Zaidat |
| 2019/0192164 | A1 | 6/2019 | Parekh et al. |
| 2019/0388112 | A1 | 12/2019 | Nguyen et al. |

FOREIGN PATENT DOCUMENTS

| | | | |
|---|---|---|---|
| WO | WO 98/53761 | A1 | 12/1998 |
| WO | WO 00/54673 | A1 | 9/2000 |
| WO | WO 03/018085 | A2 | 3/2003 |
| WO | WO 2007/103464 | A2 | 9/2007 |
| WO | WO 2011/156782 | A1 | 12/2011 |
| WO | WO 2012/162651 | A1 | 11/2012 |
| WO | WO 2014/022866 | A1 | 2/2014 |
| WO | WO 2016/109586 | A1 | 7/2016 |
| WO | WO 2016/149653 | A2 | 9/2016 |
| WO | WO 2017/156333 | A1 | 9/2017 |
| WO | WO 2018/053121 | A1 | 3/2018 |
| WO | WO 2018/106858 | A1 | 6/2018 |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International Journal of Clinical Oncology, Apr. 2004; vol. 9, Issue 2, pp. 69-73.

Zeumer, H. et al., "Local intra-arterial fibrinolytic therapy in patients with stroke: urokinase versus recombinant tissue plagminogen activator (r-TPA)," Neuroradiology, 1993; 35: pp. 159-162.

Zipfel, P. F., et al., "The Role of Complement in AMD," Inflammation and Retinal Disease: Complement Biology and Pathology, Advances in Experimental Medicine and Biology, 2010, 703, pp. 9-24.

Examination Report No. 2 for AU Application No. 2013296195, dated Jun. 27, 2017 (6 pages).

Notice of Allowance for KR 20157005602, dated Sep. 25, 2017 (3 pages).

Loh, K. et al., "Prevention and management of vision loss relating to facial filler injections." Singapore Medical Journal, 2016; 57(8): 438-443.

International Search Report and Written Opinion for International Application No. PCT/US2017/0051551, dated Dec. 15, 2017 (14 pages).

International Search Report and Written Opinion for International Application No. PCT/US2017/0052901, dated Dec. 8, 2017 (9 pages).

Bird, B. et al., "Anatomy, Head and Neck, Ophthalmic Arteries," NCBI Bookshelf, a service of the National Library of Medicine, National Institutes of Health, Oct. 27, 2018, 5 pages. www.ncbi.nlm.nih.gov/books/NBK482317/.

Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.

Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.

Schumacher, M. et al., "Intra-arterial fibrinolytic therapy in central retinal artery occlusion," Neuroradiology (1993) 35: pp. 600-605.

Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.

Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.

Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.

International Search Report and Written Opinion for corresponding PCT/US2013/053670, dated Dec. 26, 2013 (16 pp.).

Hayreh et al. "Ocular Arterial Occlusive Disorders and Carotid Artery Disease," American Academy of Ophthalmology, 2017; vol. 1, No. 1: pp. 12-18.

(56) References Cited

OTHER PUBLICATIONS

Hayreh et al. "The Ophthalmic Artery," British Journal of Ophthalmology, 1962; 46, 65: pp. 65-98.
Hayreh, S.S., "The Ophthalmic Artery III. Branches," British Journal of Ophthalmology, 1962, 46, pp. 212-247.
International Search Report and Written Opinion for International Application No. PCT/US2018/031229, dated Jul. 27, 2018 (19 pages).
Mazur et al., Catheterization and Cardiovascular Diagnosis, vol. 31, Issue 1, Abstract (1994).
Aurboonyawat et al., "Indirect Carotid-Cavernous Sinus Fistulas Treated by Transvenous Approach Through the Superior Ophthalmic Vein: A Case Report and Technical Note," Siriraj Med. J., vol. 59, pp. 191-194, 2007.
Kleintjes, "Forehead anatomy: Arterial variations and venous link of the midline forehead flap," Journal of Plastic, Reconstructive & Aesthetic Surgery, vol. 60, Issue 6, pp. 593-606, 2007.
International Search Report and Written Opinion for International Application No. PCT/US2018/014766, dated Mar. 29, 2018 (7 pages).
International Search Report and Written Opinion for International Application No. PCT/US2019/068758, dated May 29, 2020 (16 pages).
Extended European Search Report for EP 18745369.1, dated Nov. 18, 2020 (6 pages).

TREATING EYE DISEASES BY DEPLOYING A STENT

CROSS-REFERENCE TO RELATED APPLICATIONS

This patent application is a continuation of and claims the benefit to U.S. application Ser. No. 16/997,513, filed on Aug. 19, 2020, which is a continuation of and claims the benefit of priority to U.S. application Ser. No. 16/151,741, filed on Oct. 4, 2018, which issued as U.S. Pat. No. 10,779,229, on Sep. 22, 2022, and which claims the benefit of priority under 35 U.S.C. § 119 to U.S. Provisional Patent Application No. 62/568,862, filed on Oct. 6, 2017, each of which is incorporated by reference herein in its entirety.

TECHNICAL FIELD

The present disclosure relates to treating eye diseases and conditions. The present embodiments relate generally to apparatus and methods for treating medical conditions, and more specifically, to systems and methods for improving or restoring blood flow using one or more stents.

BACKGROUND

Diseases of the eye, specifically age-related macular degeneration (AMD), glaucoma, and diabetic retinopathy, affect a large percentage of the population. In the example of AMD, currently approved treatments include surgically implanting a miniature lens (VisionCare), monthly injections of the anti-cancer drug Avastin into the eye, injecting a therapeutic antibody into the eye (Macugen, pegaptanib), and/or photo or laser treatment to destroy "abnormal" blood vessels. However, these therapies are deficient in one or more aspects, necessitating improved approaches.

In a general sense, the pathogenesis of some of these eye diseases and conditions may be similar, if not the same, as those seen for cardiac diseases and for abdominal aorta conditions. However, the anatomy of the vasculature behind the eye is significantly smaller, includes more branches, and includes a more tortuous blood flow pathway than the anatomy of the vasculature of the cardiac system and the abdominal aorta. As such, treatment of such eye diseases may require increased precision by medical professionals, which may increase the time and/or cost of such treatments.

The systems, devices, and methods of the current disclosure may rectify some of the deficiencies described above or address other aspects of the prior art.

SUMMARY

Examples of the present disclosure relate to, among other things, medical devices and related methods. Each of the examples disclosed herein may include one or more of the features described in connection with any of the other disclosed examples.

In one example, a medical device may include an expandable strut structure configured for insertion within an ophthalmic artery, an internal carotid artery, or both of the ophthalmic artery and the internal carotid artery. The expandable strut structure may include a diverter element extending from the strut structure towards a free end. The diverter element may be positioned to change a direction of blood flow toward the ophthalmic artery.

Examples of the medical device may include any one or more of the following features. In a further example, the diverter element may be configured to be positioned upstream of the ophthalmic artery. The diverter element may be configured to be positioned downstream of the ophthalmic artery. The diverter element may configured to extend at an angle relative to an axis of the ophthalmic artery. The strut structure may include a first portion configured to be positioned upstream of the ophthalmic artery and a second portion configured to be positioned downstream of the ophthalmic artery. The strut structure may include a first portion configured for insertion within the internal carotid artery and the diverter element may extend from the first portion toward the ophthalmic artery. The strut structure may include a first portion configured for insertion within the internal carotid artery and a second portion configured for insertion in the ophthalmic artery. The strut structure may include at least one arm terminating in a holding element. The strut structure may further include a deflection element configured to deflect a flap of tissue positioned in at least one of the internal carotid artery, the ophthalmic artery, or within an ostium at a junction between the internal carotid artery and the ophthalmic artery. The expandable strut structure may include a strut element configured to deflect a flap of tissue in a junction between the internal carotid artery and the ophthalmic artery.

In a further aspect, a method of treating an eye of a patient may include positioning an expandable strut structure within any vessel that supplies blood to the eye or associated structures. These vessels include but are not limited to: at least one of an internal carotid artery, an ophthalmic artery, or within an ostium at a junction between the internal carotid artery and the ophthalmic artery, supra orbital artery (SOA), the supra trochlear artery (STA), the dorsal nasal artery (DNA), the middle meningeal artery (MMA), the facial arteries (FA), and branches thereof. The method may further include increasing blood flow to any artery supplying blood to the eye, including but not limited to towards the ophthalmic artery via a diverter element associated with the expandable strut structure.

Examples of the method may include any one or more of the following features. The step of increasing blood flow may result in an increase in one or more nutrients (e.g., oxygen) delivered to an eye of the patient. Treating the eye may include treating at least one disease or condition of the eye. The at least one disease or condition may include macular degeneration. The step of increasing blood flow may include altering blood flow through the strut structure via the diverter. The step of positioning the expandable strut structure may include positioning the expandable strut structure such that a first portion of the strut structure may be positioned within the internal carotid artery upstream of the ophthalmic artery, and a second portion of the structure may be positioned within the internal carotid artery downstream of the ophthalmic artery. The step of positioning the expandable strut structure may further include positioning a third portion of the stent structure within the ophthalmic artery.

In a further aspect, a method of altering blood flow through the vasculature of an eye may include disrupting an eddy flow of blood in any artery that supplies blood to the eye, including but not limited to at least one of an ophthalmic artery, an internal carotid artery, or both of the ophthalmic artery and the internal carotid artery via a diverter element of an expandable strut structure positioned within the vasculature of the eye.

Examples of the method may further include any one or more of the following features. The method may include treating at least one disease or condition of the eye. The at least one disease or condition may include macular degeneration.

In a further aspect, a method of treating an eye of a patient may include positioning an expandable strut structure within at least one of an internal carotid artery, an ophthalmic artery, or an ostium at a junction between the internal carotid artery and the ophthalmic artery. Additionally, the method may include directing blood flow towards the ophthalmic artery via a diverter element associated with the expandable strut structure.

Examples of the method may further include any one or more of the following features. The step of directing blood flow may result in an increase in oxygen delivery to the eye of the patient. Treating the eye may include treating at least one disease or condition of the eye. The at least one disease or condition may include macular degeneration. The step of directing blood flow may include altering blood flow through the strut structure via the diverter. The step of positioning the expandable strut structure may include positioning the expandable strut structure such that a first portion of the strut structure may be positioned within the internal carotid artery upstream of the ophthalmic artery, and a second portion of the structure may be positioned within the internal carotid artery downstream of the ophthalmic artery. The step of positioning the expandable strut structure may further include positioning a third portion of the stent structure within the ophthalmic artery. The diverter element may extend from the first portion of the strut structure towards the ophthalmic artery. The diverter element may include a first end coupled with the expandable strut structure and a second end free form contact with the expandable strut structure. The step of directing blood flow may include directing blood flow at an angle with respect to an axis of the ophthalmic artery via the diverter element.

In a further aspect, a method of treating an eye of a patient may include positioning an expandable frustoconical strut structure within an ostium at a junction between an internal carotid artery and an ophthalmic artery. Additionally, the method may include directing blood flow within the ophthalmic artery via the expandable frustoconical strut structure.

Examples of the method may further include any one or more of the following features. The step of positioning the expandable frustoconical strut structure may include positioning an entirety of the expandable frustoconical strut structure within the ostium. The step of positioning the expandable frustoconical strut structure may include locating the expandable frustoconical strut structure such that no portion of the expandable frustoconical strut structure is located within the internal carotid artery. The expandable frustoconical strut structure may include a first end having a first cross-sectional dimension and a second end having a second cross-sectional dimension larger than the first cross-sectional dimension, and the step of positioning the expandable frustoconical strut structure may include positioning the first end distally of the second end within the ostium. The step of directing blood flow within the ophthalmic artery via the expandable frustoconical strut structure may include directing blood flow towards the ophthalmic artery via a diverter element associated with the expandable frustoconical strut structure. The step of directing blood flow may include altering a direction of blood flow through the strut structure via the diverter element. The step of directing blood flow may result in an increase in oxygen delivery to the eye of the patient. Treating the eye may include treating at least one disease or condition of the eye, wherein the at least one disease or condition may include macular degeneration.

In a further aspect, a method of treating an eye of a patient may include positioning an expandable strut structure within an arterial system of the patient. Additionally, the step of positioning the expandable strut structure may include positioning a majority of the expandable strut structure within an internal carotid artery of the patient and positioning a strut of the expandable strut structure within at least one of an ophthalmic artery of the patient or an ostium between the ophthalmic artery and the internal carotid artery of the patient. Additionally, the method may include deflecting tissue via the strut.

Examples of the method may further include any one or more of the following features. The strut may be the only portion of the expandable strut structure located within the at least one of the ophthalmic artery or the ostium. The strut may include at least one of an increased thickness or an increased rigidity relative to a remainder of the expandable strut structure. Treating the eye may include treating at least one disease or condition of the eye, and the at least one disease or condition may include macular degeneration.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body. Further, as used herein, dimensions measured in French, abbreviated Fr or F, are three times the size of the same dimension as measured in mm. Thus, a 3-mm diameter catheter is 9 French in diameter.

Figure 1:
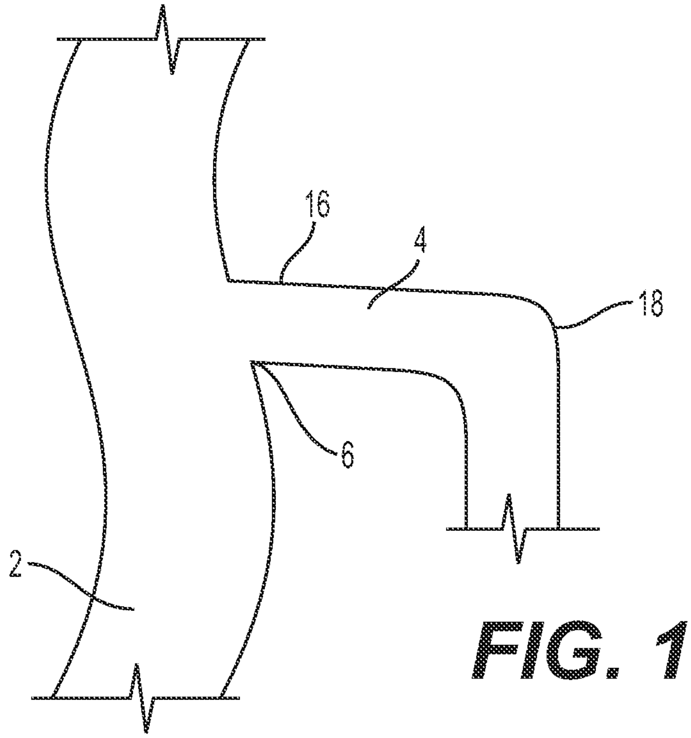
FIGS. 1 and 2 illustrate an anatomical location of interest relating to the eye of a patient.
Figure 2:
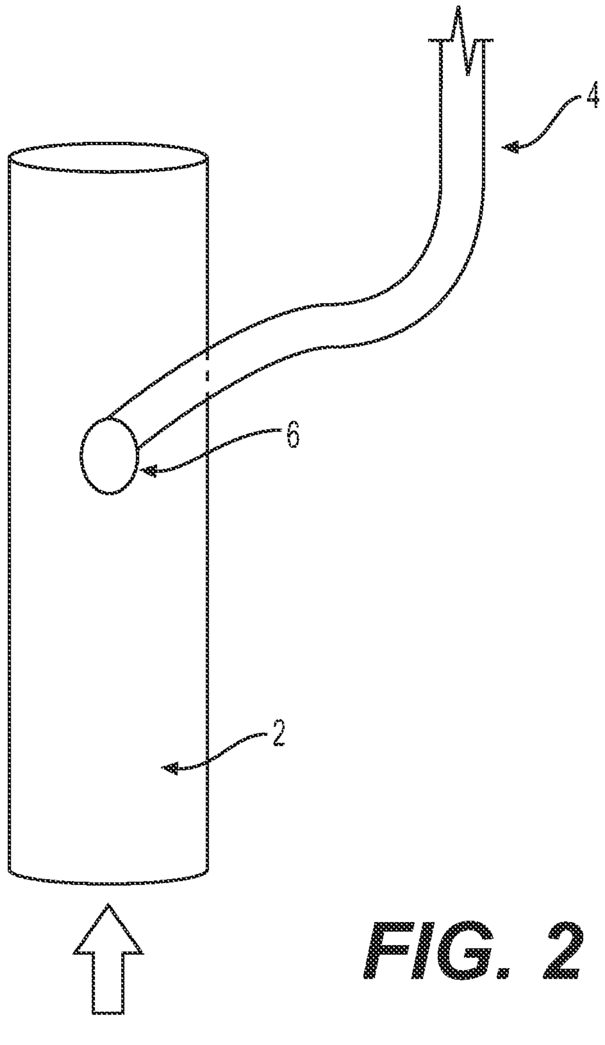

FIGS. 1 and 2 illustrate an anatomical area of interest relating to an eye of a patient. For example, such an anatomical area of interest may include all of the vasculature in the fluid flow path to and from the eye, the rear of the eye, portions of the eye, or regions near the eye. By way of example only, as shown in FIG. 1, the vasculature of the eye includes the Internal Carotid Artery (ICA) 2, the Ophthalmic Artery (OA) 4, and the junction 6 between the ICA 2 and the OA 4, which is also referred to as the ostium. As shown, OA 4 is illustrated as extending generally at a right angle relative to the ICA 2. In other arrangements, however, the OA 4 extends at an acute angle relative to ICA 2. In some patients, a flap of tissue (not shown), may extend between OA 4 and ICA 2. That is, in some arrangements, the flap of tissue may be positioned in junction 6. Additional areas of the anatomy may include the vascular system which is commonly referred to as the terminal branches (not shown). These areas include, but are not limited to, the Supra Orbital Artery (SOA), the Supra Trochlear Artery (STA), the Dorsal Nasal Artery (DNA), and the Facial Arteries (FA). It is noted that the anatomical structures described herein may additionally be referred to by other terminology. *Hayreh et al.* (Brit. J. Ophthal., 46, 65 (1962)), the entirety of which is herein incorporated by reference, describes the anatomy relating to the eye as including the ICA (I), the OA (O) branching off of the ICA in a portion called the "short limb" (S); "angle a" (AA) as a distinctive turn in the OA near the end of the OA near the ICA; the "long limb" (LL) as the portion of the OA before it penetrates into the dural sheath; "angle b"; and then the distal portion of the OA as it extends to the eye. The junction (J) between the ICA and the OA includes the ostium (OS). One skilled in the art will readily recognize that these are typical or common structures; not all patients/humans have these exact same structures, e.g., there are human population variations.

Diseases and conditions of the eye (e.g., AMD, glaucoma, diabetic retinopathy etc.) may result in decreased blood flow to and around the eye, which is believed to contribute to oxygen depletion in and around the eye. Decreased blood flow to and around the eye may also contribute to depletion of one or more additional nutrients such as, for example, glucose or amino acids, as well as an increase waste products in the eye. According to examples of the present disclosure, diseases and conditions of the eye may be directly mediated by improved blood flow to the vasculature of the eye (e.g., the posterior of the eye). For example, the systems, devices, and methods described herein may restore or increase the amount of oxygen (and/or other nutrients) that reaches the eye or an eye area which may include removing or opening a blockage (or partial blockage) in one or more vascular systems that support the eye. Opening a blockage or partial blockage may include increasing or restoring blood flow to or around the eye. Increasing blood flow may include, but is not limited to, increasing the blood flow rate. That is, examples of the present disclosure may be directed to one or more intravascular medical devices and/or methods intended or configured to sufficiently unblock or at least partially restore blood flow in a blocked or partially blocked artery such that oxygen content (and/or the content of other nutrients) is increased distal to the blockage, as well as improving the removal of waste products that are also distal to the blockage. For example, in some arrangements, the present disclosure is directed to devices and methods for restoring blood flow through the ostium or junction 6. In additional arrangements, the disclosure is directed to using such devices and methods to restore or increase blood flow and/or or restore or increase oxygen levels, to the eye or a portion thereof. Restoring or increasing oxygen flow may include using the devices and methods described herein, or equivalent devices and methods, but is not to be limited thereby.

For example, stents may be inserted (e.g., percutaneously) into an anatomical vessel or duct for various purposes. Stents may maintain or restore patency in a formerly blocked or constricted passageway (e.g., following a balloon angioplasty procedure or an atherectomy procedure). A stent of the present disclosure, or a portion thereof, may be sized to conform to the anatomy in which it is placed. Without intending to limit the scope of the present disclosure, exemplary stent diameters may range from less than about 1.5 mm to about 3 mm for stents or portions of a stent that are placed in the OA 4. A stent or a portion of a stent in the ICA 2 is typically larger. Exemplary stent length may range from 0.5 mm or longer for stents or portions of a stent that are placed in the OA 4. A stent or a portion of a stent in the ICA 2 is typically longer.

Figure 3:
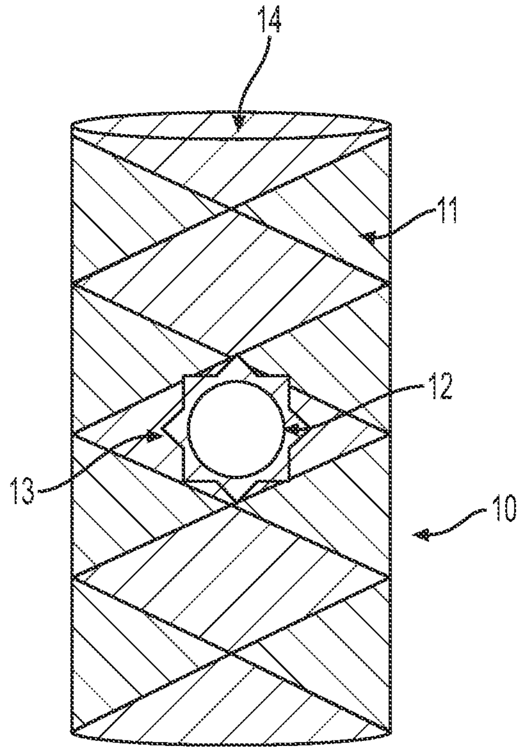
FIG. 3 illustrates an exemplary stent, according to aspects of the present disclosure.

As shown in FIG. 3, an exemplary stent 10 may include a plurality or framework of struts 11 which may be adapted and configured for placement in the ICA 2 and/or the OA 4. Stent 10 may be either self-expandable and/or non-self-expandable (e.g., expandable via a balloon or other mechanical device). For example, self-expanding stents may be delivered to a target site in a compressed configuration and subsequently expanded by removing a delivery sheath/catheter, removing trigger wires, and/or releasing diameter reducing ties. Such self-expanding stents may expand primarily based on their own expansive force without the need for further mechanical expansion. Optionally, stent 10 may be comprised of a shape-memory alloy such as Nitinol. Shape-memory alloy may be employed to cause the stent 10 to return to a predetermined configuration (e.g., expanded configuration) upon removal of the sheath or other device maintaining the stent 10 in its pre-deployment configuration. Non-self-expanding struts may be delivered to a target site in a compressed configuration and expanded upon the application of an outward radial force. For example, a balloon (not shown) may be positioned within a lumen 14 of stent 10 and inflated so as to expand stent 10.

As noted above, one or more trigger wires (not shown) may be used to restrain a "Z-stent" or Gianturco style stent comprising a series of substantially straight segments interconnected by a series of bent segments. The trigger wires may be disposed through, and pull upon, the bent segments to pull the stent 10 closely against a delivery catheter. Optionally, trigger wires may be used in conjunction with different stent designs, such as cannula-cut stents having relatively acute or pointed bends. The designs of cannula-cut stents may facilitate compression of the stent to a relatively small delivery profile due to the tight bends of the apices.

With such stents, the trigger wires may be looped around one or more vertices formed beneath the proximal and/or distal apices, e.g., a location where an individual apex splits into two separate strut segments.

Optionally, stent 10 may include a cover (not shown) thereon. The cover of stent 10 may be comprised of or coated with a lubricious material so as to facilitate movement between stent 10, a delivery catheter, and/or a vessel wall. Additionally, the cover may be positioned on an internal surface, an external surface, or both the internal surface and the external surface of stent 10. In some arrangements, stent 10 may be embedded within the cover. Further, such a coating or cover may be substance eluting (e.g., drug-eluting). For example, such a drug-eluting coating or cover may release any one or more drugs or substances for the treatment of restenosis. Additionally, such a cover or coating may only be provided on one or more portions of stent 10. For example, in some arrangements, such a cover or coating may be positioned on a diverter (discussed below) of stent 10. The cover or coating may optionally comprise expanded polytetrafluoroethylene (ePTFE) or any other appropriate material. Stent 10, or the cover thereof, may also include one of more markers, typically radiopaque markers. For example, stent 10 and/or the cover thereof may be coated or impregnated with one or more radiopaque markers 13 to aid in the proper placement of stent 10 within the target anatomy, e.g., the ostium or junction 6 of ICA 2 and OA 4. Additionally, stent 10 may comprise an opening or port 12 extending through a circumferential surface thereof. As shown, port 12 may be free from stent struts 11 and may be unobscured by a stent covering. Port 12 may be dimensionally compatible with an opening into the OA 4 at the ostium 6 such that the OA 4 will be unobscured by stent 10 once it is placed within the vasculature. In other words, port 12 may be sized and shaped so as to surround the opening into the OA 4 at the ostium 6. In some arrangements, port 12 may be generally circular or rounded, as shown in FIG. 3. In additional arrangements, port 12 may extend circumferentially about the entire circumference of stent 10. In such an arrangement, a first portion and a second portion of stent 10 may be coupled together via one or more struts thereby forming a circumferential port, unobscured by a stent covering, therebetween.

The use of catheter delivery systems for positioning and deploying therapeutic devices, such as balloons, stents and embolic devices, in the vasculature of the human body has become a standard procedure for treating endovascular diseases. It has been found that such devices are particularly useful in treating areas where traditional operational procedures are impossible or pose a great risk to the patient. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Figure 4:
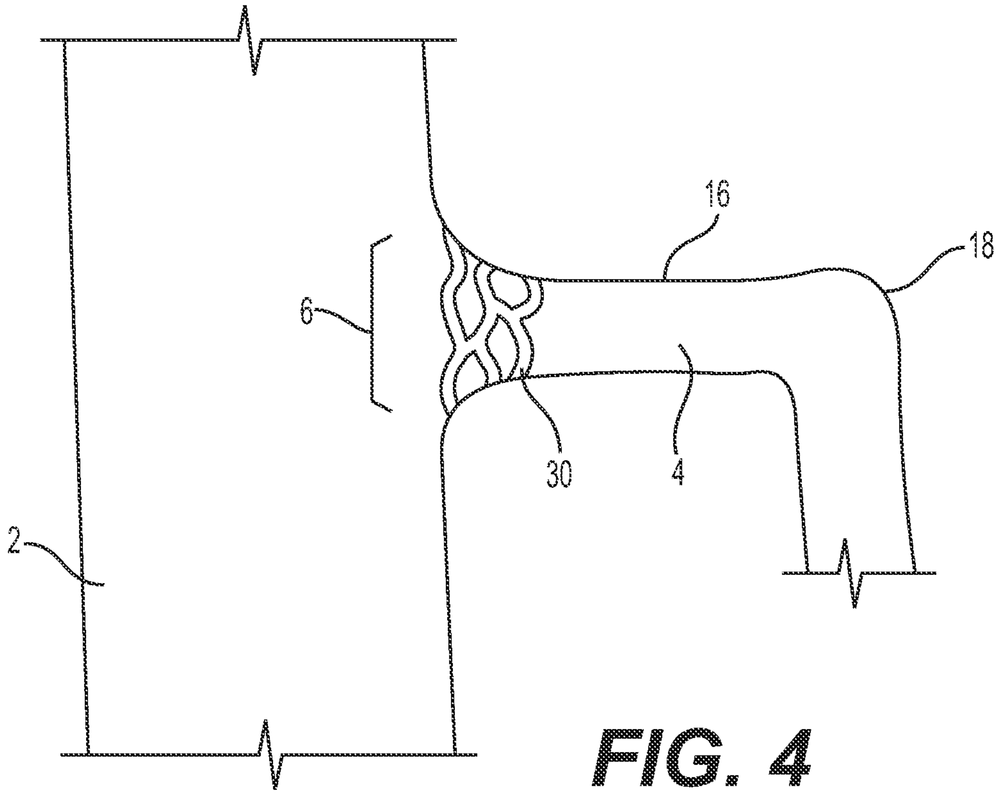
FIGS. 4-11 illustrate various features of the exemplary stents, according to aspects of the present disclosure.

As noted above, the OA 4, particularly the portion of the OA 4 near the ICA 2 (e.g., ostium or junction 6) presents a challenging anatomy for stent 10 placement and function. The anatomy of junction 6 typically comprises a very sharp angle. Further, the OA 4 comprises a short section near the ICA 2, called the short limb 16, followed by a sharp bend, called angle A 18 (FIG. 4). Often, prior art stents (e.g., aortic stents) lack the desired sealing ability at either end of the stent, in other words, they lack the desired radial force against the arterial wall at the stent ends. Also, such devices often include a relatively large profile which may not be appropriately sized for insertion in the small and tortuous vasculature of the eye. Finally, such stents often have relatively acute points that may prevent them from being used in acute angle anatomies for fear of trauma with the artery wall after an extended amount of time in the patient. In some arrangements, a generally nonsymmetrical stent 10 having at least one relatively rounded apex that is less invasive in an expanded state than stents with more acute apices may alleviate the above problems, while providing an improved compliance to the ICA 2 and OA 4, and increased radial force if used as a sealing and/or alignment stent, as well as a desirable ability to be crimped to a readily introducible diameter.

A portion of such a stent 10 may include a first width that is less than a second width of the axial opening of the retaining member. The axial opening may extend longitudinally between first and second ends of the main body of the retaining member.

In one arrangement, the stent 10 may comprise at least one coupling portion comprising a longitudinal strut portion having the first width that is less than the second width of the axial opening of the retaining member. The coupling portion may extend proximally from a proximal apex of the stent 10. The coupling portion may include a projection. In one example, the longitudinal strut portion and the projection of the coupling portion may collectively may form a "t" shape. The lateral projection may be disposed proximal to the first end of the main body of the retaining member when the stent is restrained.

The present disclosure relates generally to stents for use in body vessels to treat medical conditions, and more specifically, to treat conditions of the eye and/or vasculature supplying blood flow to the eye.

In particular, this present disclosure relates to a stent 10 having opposing sets of curved apices, where the curved section of one set of apices has a radius of curvature that is greater than the curved section of another set of apices, and may present a lower profile than conventional stents. This configuration presents an asymmetrical stent. Specifically, embodiments of the stents disclosed herein may maintain a low profile while improving compliance with highly tortuous anatomy (such as, for example, the anatomy found in the region between the ICA 2 and the OA 4) while providing improved radial sealing force compared to some current devices. In another example, one or more stents described herein may provide support and spacing within the larger context of a stent or stent-graft device that will allow, for example, placement of ancillary stents and/or stent-grafts.

Examples of the present disclosure may include a stent 10 that includes at least one proximal apex and at least one distal apex connected with the proximal apices by a plurality of generally straight portions; where each proximal apex includes a first curved portion and each distal apex comprises a second curved portion; where the first curved portion and the second curved portion each includes at least one radius of curvature, and the radius of curvature of at least one of the proximal apices is greater than the radius of curvature of at least one of the distal apices.

In another arrangement, examples of the present disclosure may include at least one wire formed into a stent 10 and including a ring of alternating opposed, generally curved apices where a radius of curvature of a plurality of the apices in a first direction is greater than a radius of curvature of the apices in an opposite direction. Advantageously, the rounded apices may provide atraumatic contact with a vessel, while the combination of more rounded and less rounded apices provides for a low-profile stent that includes desirable compressibility during introduction and desirable compliance and sealing profiles when deployed in a vessel.

In some examples, the present disclosure may be directed to an intravascular stent 10 that has a pattern or configuration that permits the stent 10 to be tightly compressed or crimped onto a catheter to provide an extremely low profile and to prevent relative movement between the stent 10 and the catheter. Such a stent 10 also may be highly flexible along its longitudinal axis to facilitate delivery through tortuous body lumens, but which is stiff and stable enough radially in its expanded condition to maintain the patency of a body lumen such as an artery when the stent is implanted therein.

In some examples of the present disclosure, a stent 10 may include a plurality of cylindrical rings that are interconnected to form the stent 10. Such a stent may be mounted on a balloon catheter, if it is balloon expandable, or mounted on or in a catheter without a balloon, if it is self-expanding.

Each of the cylindrical rings making up the disclosed stents 10 may have a proximal end and a distal end and a cylindrical outer wall surface that extends between the proximal end and the distal end of the cylindrical ring. Generally, the cylindrical rings have a serpentine or undulating shape which includes at least one U-shaped element, and typically each ring has more than one U-shaped element. The cylindrical rings may be interconnected by at least one undulating link which may attach one cylindrical ring to an adjacent cylindrical ring. The undulating links may be highly flexible and allow the stent 10 to be highly flexible along its longitudinal axis. At least some of the undulating links have a curved portion that extends transverse to the stent longitudinal axis for a predetermined distance that coincides with one of the U-shaped elements. More specifically, the curved portion extends in a transverse manner such that it would intersect with the corresponding U-shaped element, however, the corresponding U-shaped element is shorter in length than other U-shaped elements in the same ring. Thus, when the stent 10 is compressed or crimped onto the catheter, the curved portions do not overlap or intersect with the adjacent U-shaped element since that element is shorter in length than similar U-shaped elements in the particular ring. In this manner, the stent 10 can be compressed or crimped to a much tighter or smaller diameter onto the catheter which permits low profile delivery as well as a tight gripping force on the catheter to reduce the likelihood of movement between the stent and the catheter during delivery and prior to implanting the stent 10 in the vessel.

The undulating links may take various configurations but in general have an undulating or serpentine shape. The undulating links can include bends connected by substantially straight portions wherein the substantially straight portions are substantially perpendicular to the stent longitudinal axis.

Not only do the undulating links that interconnect the cylindrical rings provide flexibility to the stent, but the positioning of the links also enhances the flexibility by allowing uniform flexibility when the stent 10 is bent in any direction along its longitudinal axis. Uniform flexibility along the stent 10 derives in part from the links of one ring being circumferentially offset from the links in an adjacent ring. Further, the cylindrical rings are configured to provide flexibility to the stent 10 in that portions of the rings can flex or bend and tip outwardly as the stent 10 is delivered through a tortuous vessel.

The cylindrical rings typically are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that at least a portion of the undulating links is positioned within one of the valleys and it attaches the valley to an adjacent peak.

While the cylindrical rings and undulating links generally are not separate structures (e.g., they may include a one-piece monolithic stent 10 structure), they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resemble such configuration. The U's, W's and Y's promote flexibility in the stent primarily by flexing and by tipping radially outwardly as the stent 10 is delivered through a tortuous vessel.

A stent 10 of the present disclosure can be made in several ways. In one embodiment, metallic rings are cut by a laser using conventional laser cutting procedures. The rings are then mounted on an inner polymeric tube which has been pre-mounted on a Teflon mandrel. After the rings have been mounted and positioned on the inner polymeric tube, an outer polymeric tube is mounted over the metallic rings and the inner polymeric tube. A shrink tubing is then mounted over the outer polymeric tube and it is subjected to laser bonding so that the shrink tubing contracts and applies pressure to the outer polymeric tube causing it to compress against the metallic rings and the inner polymeric tube. Further, heat from the laser causes the outer and inner polymeric tubes to partially melt and fuse together. An appropriate bonding agent can be used to help adhere the inner and outer tubes together. The shrink tubing and the supporting Teflon mandrel are removed and the stent pattern is then formed by a laser to remove unwanted portions of the polymer material, so that a pattern of metallic rings encased by the polymer material are attached to each other by polymeric links as previously disclosed.

According to a further arrangement, an exemplary stent 10 may be made by first dip coating a mandrel into a polymer which corresponds to the inner polymeric material. The metallic rings, which previously were laser cut from a tube, are mounted on the inner polymer material and positioned to form the stent pattern. The outer layer or outer polymer material may be deposited over the metal rings either by spray coating or by dip coating the outer polymeric material over the rings and the inner polymeric material. Then, the mandrel is removed and the unwanted portions of the polymers can be machined by using laser cutting as previously described.

Examples of the present disclosure may include at least one stent 10 adapted and configured to the anatomy of the vascular system that supplies blood flow to the eye. In some examples, as noted above, the vascular system includes the ICA 2, the OA 4, or combinations or portions thereof. In some examples, at least one stent 10 is configured for insertion into one or more segments of the anatomy selected from the group including the short limb 16 of the OA 4, angle A 18 of the OA 4, the ostium, the junction 6 between the OA 4 and the ICA 2, the portions of the ICA 2 upstream and downstream of the OA 4, and combinations thereof.

In some examples, the stent 10 is a single or unitary structure (e.g., one-piece monolithic structure) configured to the anatomy of the OA 4, a portion of the OA 4, the ICA 2, or combinations thereof. For example, a single stent 10 or a portion thereof may be adapted to conform to the anatomy of the short limb 16. In another example, a single stent or a portion thereof may be adapted to conform to the anatomy of both the ICA 2 and the OA 4, e.g., in the junction 6 between the ICA 2 and the OA 4.

In some embodiments, the stent 10 is a multiple-piece structure or multi-segment structure configured to the anatomy of the OA 4, a portion of the OA 4, the ICA 2, or combinations thereof. For example, a stent according to this embodiment, or a portion thereof, may be adapted to conform to the anatomy of the short limb 16. In another example, a stent of this embodiment, or a portion thereof, may be adapted to conform to the anatomy of both the ICA 2 and the OA 4, e.g., in the junction between the ICA and the OA.

FIG. 4 shows stent 30 configured for insertion within the ostium of the OA 4. Some embodiments of stent 30 may be configured to open the OA 4 or the flap (not shown) in the junction 6 between the ICA 2 and the OA 4. As shown in FIG. 4, stent 30 has a proximal end (closer to the ICA 2) that is wider than a distal end (within OA 4). Stent 30 therefore has a frustoconical, or tapered shaped. The proximal end is dimensioned (e.g., has a diameter) so as to be seated at the ostium or junction 6 between the OA 4 and the ICA 2. The distal end is dimensioned (e.g., has a diameter) so as to be seated in the OA 4. Stent 30 does not extend into the ICA 2.

Figure 5:
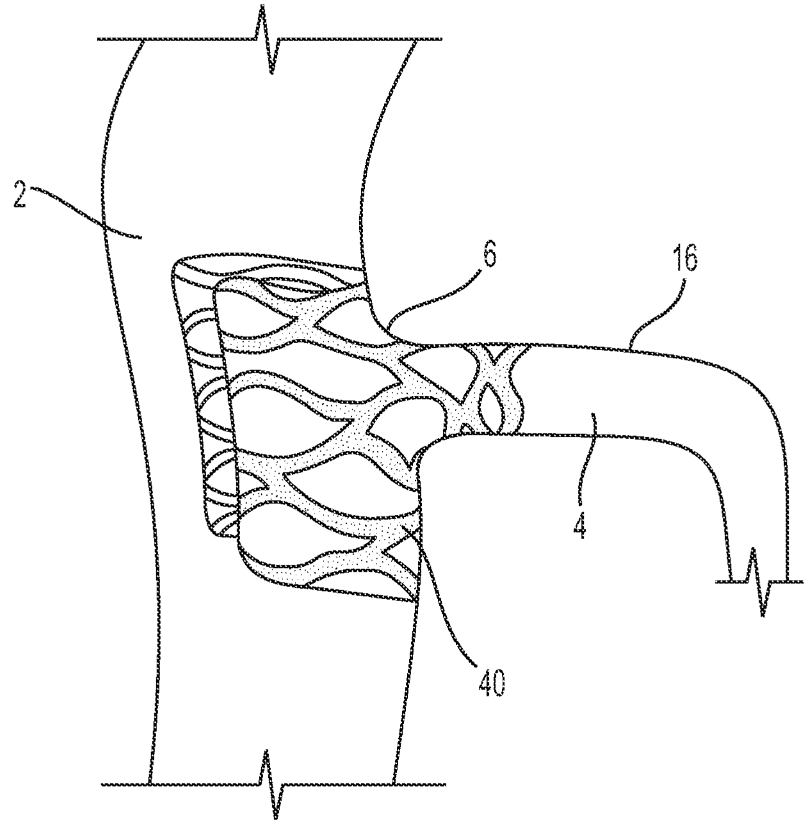

FIG. 5 shows a stent 40 configured for insertion within both the ICA 2 and the OA 4, with strut or stent elements that span the junction 6. That is, at least a distal portion of stent 40 is dimensioned (e.g., has a diameter) so as to be seated in the OA 4, while at least a proximal portion of stent 40 is dimensioned (e.g., has a diameter) so as to be seated in the ICA 2.

Figure 6:
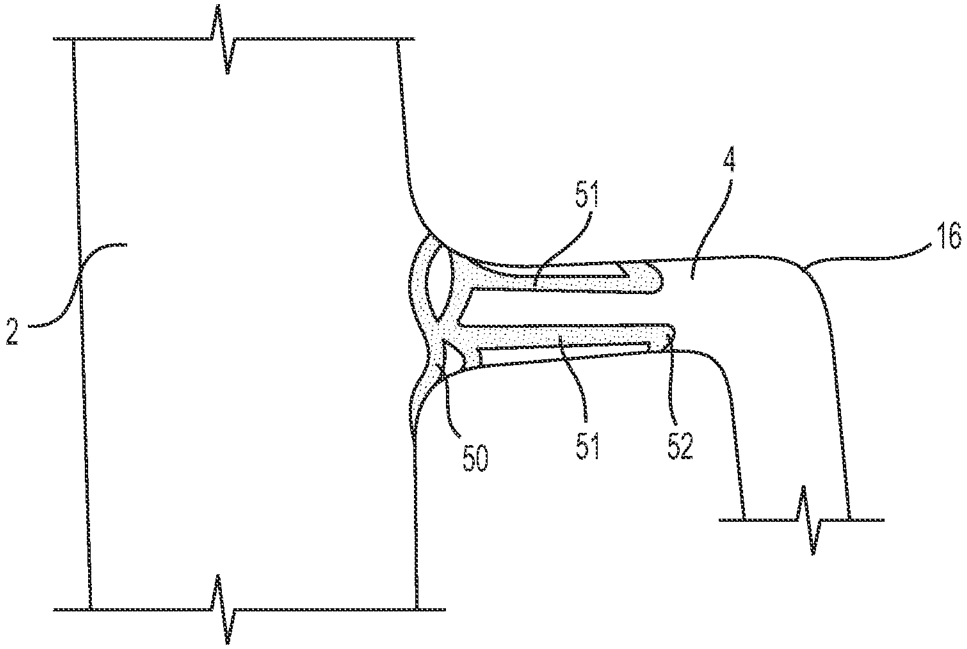

FIG. 6 shows a stent 50 configured for insertion within the OA 4, with struts or arms 51 that extend into the short limb 16. FIG. 6 further illustrates an additional feature that may be added to any stent of the present disclosure, namely one or more holding elements 52 or barbs, configured to hold or retrain the stent 50 in place. As shown, stent 50 incudes a proximal end (closer to the ICA 2) that is wider than a distal end (within OA 4). Stent 50 therefore has a frustoconical, or tapered shaped. The proximal end is dimensioned (e.g., has a diameter) so as to be seated at the ostium or junction 6 between the OA 4 and the ICA 2. The distal end is dimensioned (e.g., has a diameter) so as to be seated in the OA 4. Stent 50 does not extend into the ICA 2. Further, each arm 51 may include one end coupled, joined, or otherwise formed with stent 50 and another end free from connection to stent 50 or another arm 51. A longitudinal extent (e.g., in the direction of the OA 4) of arms 51 is longer than a longitudinal extend of stent 50. While only two arms 51 are shown, the disclosure is not so limited. Rather in some arrangements any number of arms 51, equidistantly or non-equidistantly spaced about a periphery of stent 50, may be used.

Figure 7:
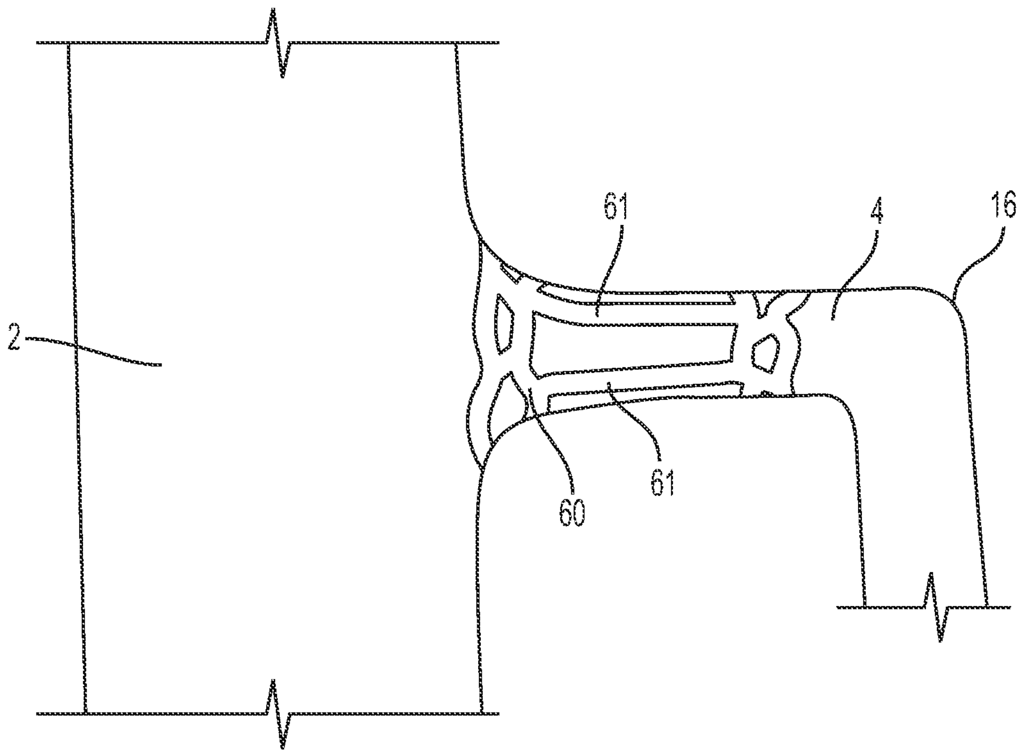

FIG. 7 shows stent 60 configured for insertion within the OA 4 and including one or more extensions or longer struts 61 that allow a portion of the stent 60 to extend further into the short limb 16. That is, multiple segments or portions of stent 60 may be connected to one another via struts 61, as shown. The proximal end (closer to ICA 2) is dimensioned (e.g., has a diameter) so as to be seated at the ostium or junction 6 between the OA 4 and the ICA 2. The distal end (closer to the OA 4) is dimensioned (e.g., has a diameter) so as to be seated in the OA 4. Stent 60 does not extend into the ICA 2. While only two struts 61 are shown, the disclosure is not so limited. Rather in some arrangements any number of struts 61, equidistantly or non-equidistantly spaced about a periphery of stent 60, may be used. As shown, a longitudinal extent (e.g., in the direction of the OA 4) of struts 61 may be longer than the longitudinal extent of the multiple portions or segments of strut 60.

Figure 8:
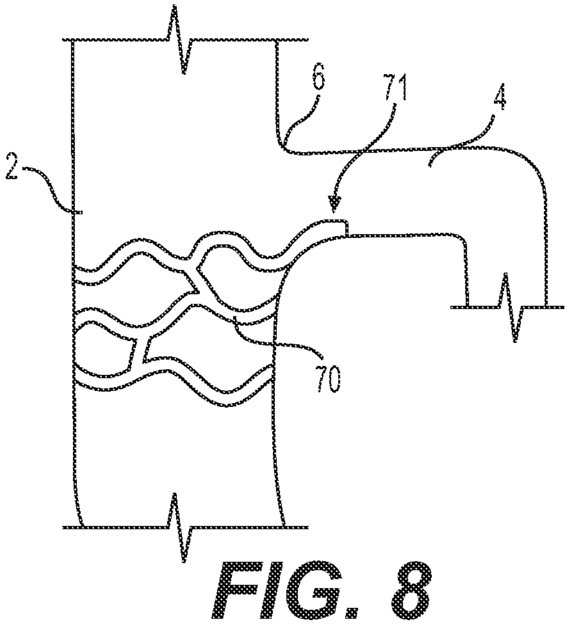

FIG. 8 shows a stent 70 configured for insertion within the ICA 2, and including a stent element 71 configured to open or hold down the flap (not shown) in the OA 4 that is on the proximal end (e.g., the end closest to ICA 2) of the OA 4. That is, stent element 71 may be positioned so as to bias (e.g., deflect) such a flap in a manner to further increase an opening side of the ostium in the junction 6. As shown, a thickness (and/or rigidity) of stent element 71 may be larger than a thickness of a remainder of stent 70. Optionally, stent element 71 may be the only portion of stent 70 extending into the OA 4. In other arrangements, stent 70 may include multiple stent elements 71. While stent element 71 is shown at a downstream end of a remainder of stent 70, in other arrangements, stent element 71 may be arranged upstream of a remainder of stent 70.

Figure 9:
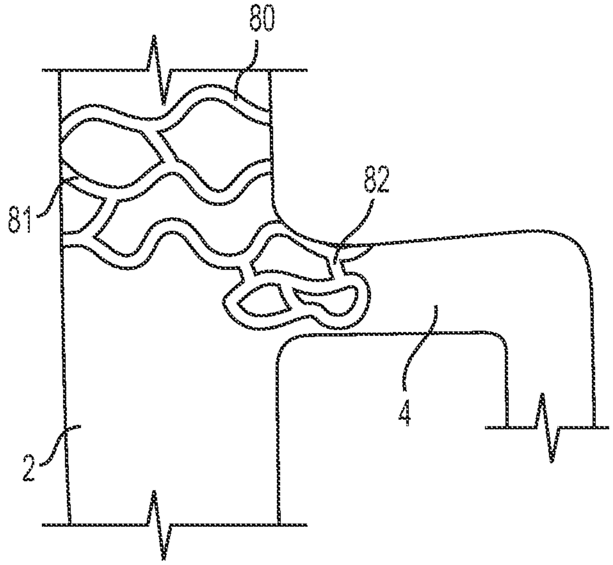

FIG. 9 shows a stent 80 configured for insertion within the ICA 2 and including a portion 81 configured for insertion within the ICA 2 and a portion 82 configured for insertion within the OA 4. That is, stent 80 at least partially spans the junction between the ICA 2 and the OA 4. As shown, at least a portion of portion 82 may remain within ICA 2. Additionally, at least some of the struts of portion 82 may be spaced closer to one another than at least some of the struts of portion 81. Accordingly, stent 80 may have a varied density of struts. In other arrangements, a density of struts of stent 80 may be continuous.

Figure 10:
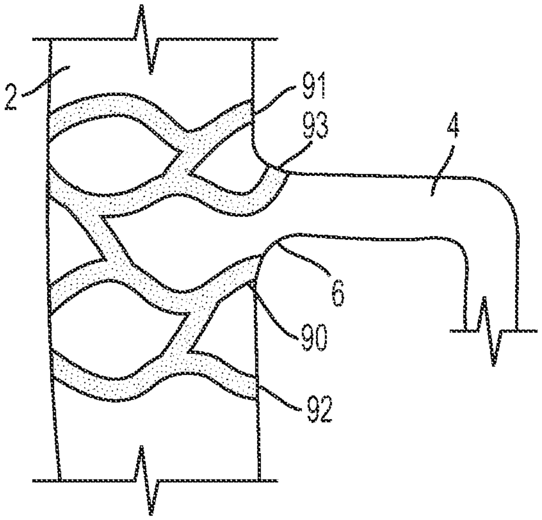
Figure 11:
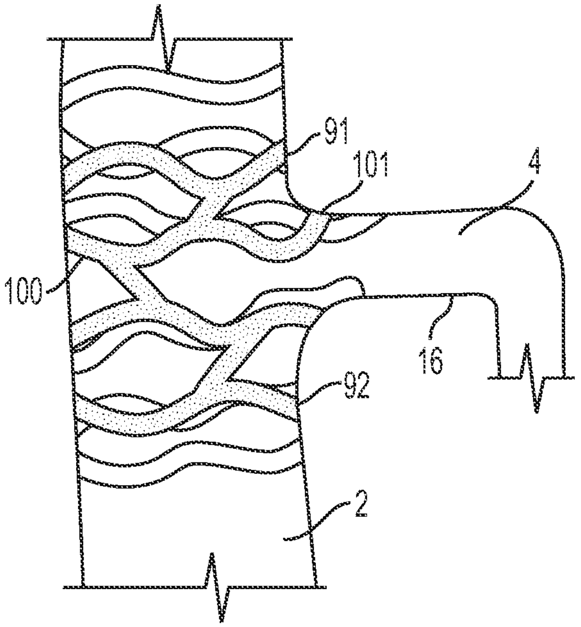

FIG. 10 illustrates a stent 90 configured for insertion within the ICA 2 and including a portion 91 in the ICA 2 that is distal to (e.g., downstream of) the OA 4 and a portion 92 in the ICA 2 that is proximal to (e.g., upstream) the OA 4. FIG. 10 also shows one or more stent struts 93 (optional) that extend at least partially into the ostium at the junction 6 between the ICA 2 and the OA 4. Similarly, FIG. 11 illustrates a stent 100 configured for insertion within the ICA 2 and including a portion 91 that is distal to (e.g., downstream of) the OA 4 and a portion 92 that is proximal to (e.g., upstream) the OA 4. As shown, stent 100 may further include one or more stent struts 101 (optional) that extend into the short limb 16. The one or more stent struts 101 may include a free end positioned distally of the junction 6 and uncoupled from a remainder of stent 100.

Figure 12:
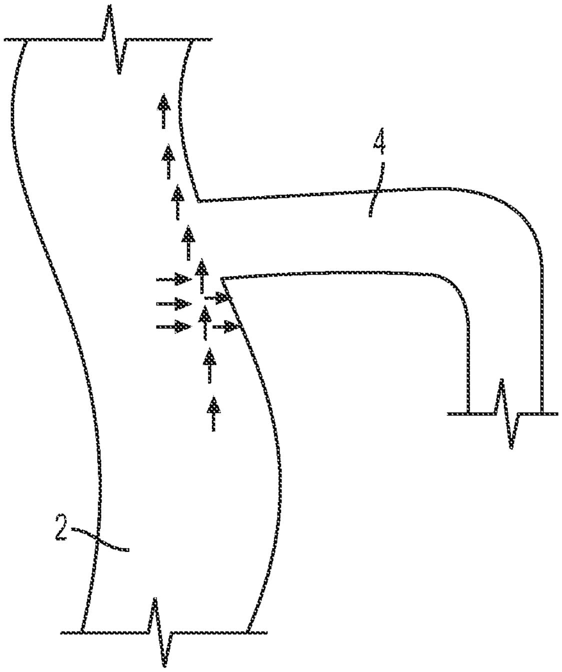
FIG. 12 illustrates an eddy in a blood flow path of the vasculature of the eye.

Any of the stents described herein may optionally include one or more components to adjust blood flow between the ICA 2 and the OA 4. For example, as shown in FIG. 12, an exemplary eddy blood flow pattern in the area between the ICA 2 and the OA 4 is illustrated. As can be seen, during natural blood flow through the vasculature, a circular or non-linear movement or redirection of blood may occur (e.g., an eddy) which may alter or diminish the blood flow supply flowing from the ICA 2 to the OA 4. As shown, the eddy may be located upstream of the OA 4 and along a wall of the ICA 2. For example, such an eddy may reduce a blood flow rate or amount of blood that flows from the ICA 2 through the OA 4, and then continues on to the eye. As noted above, a reduced amount or rate of blood flow may also result in reduced oxygen supply to the eye, which may further contribute to the eye diseases and conditions noted above. Further, any one or more obstructions (e.g., partial and/or complete obstructions, narrowing of a vessel, and/or lesions) may further contribute to reduced blood flow from the ICA 2 through the OA 4. Accordingly, any one or more of the examples herein described may further include a structure or element configured to guide or direct flow in a desired manner.

For example, a diverter element or structure may be used in conjunction with any of the stents disclosed herein. Each diverter element may include a strut terminating in a free end. That is, in one embodiment, such an element may have a first end coupled to, joined with, or formed monolithically as a one-piece structure with a remainder of any of the disclosed stents herein, and a second end, opposite the first end, uncoupled, unjoined, or otherwise free from contact with a remainder of any of the disclosed stents herein. Moreover, such a diverter element may extend at an angle relative to the ophthalmic artery. As used herein, a diverter may include one or more element(s) or structure(s) that channel blood flow through the lumen 14 defined by the stent body or an element or structure that is used to bypass one or more portions of the stent. In other words, a diverter may mediate, affect, and/or alter blood flow, specifically eddies, so as to improve or increase a blood flow rate and/or an amount of blood flowing from the ICA 2 to the OA 4 and/or promote and/or optimize the laminar flow of blood through the stent lumen 14 and/or the vessel within which the stent is inserted. That is, a diverter may reduce the amount or impact of eddies.

Figure 13:
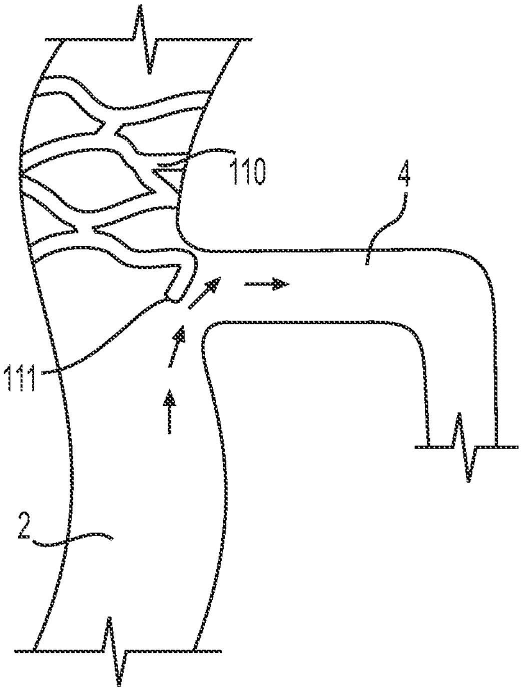
FIGS. 13-17 illustrate further features of the exemplary stents of the present disclosure.
Figure 14:
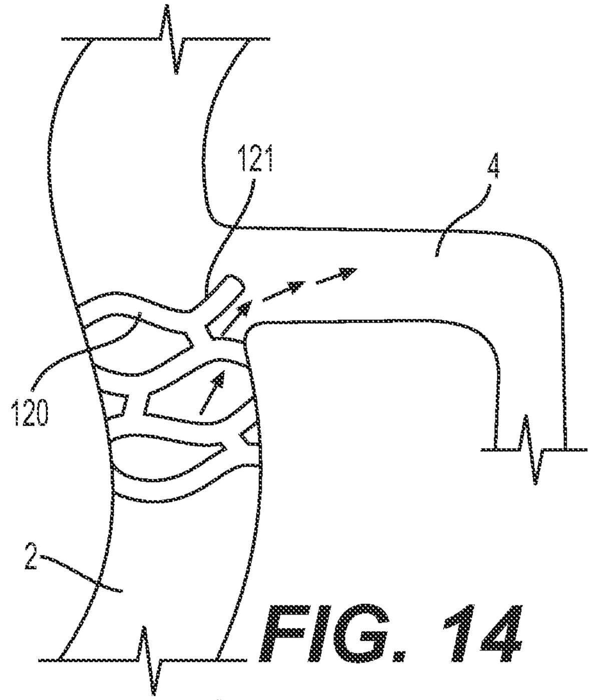

FIG. 13 illustrates a stent 110 including a diverter 111 which may change or alter the blood flow dynamics between the ICA 2 and the OA 4, preferably increasing the amount of blood entering the OA 4. That is, as blood flow travels from the ICA 2 toward the OA 4, the blood flow may impact or be disrupted by re-diverter 111 which may guide or otherwise facilitate the flow of blood from ICA 2 to OA 4. Diverter 111 may include an extension of a proximalmost strut of stent 110, and has an atraumatic shape so as to not cause damage to surrounding blood vessel walls. Diverter 111 also may include a dimension (e.g., thickness, width, etc.) that is larger than the strut from which it extends. In this way, it may present sufficient surface area facing the oncoming blood flow to deviate a desired amount of flow. In a FIG. 14 illustrates a further arrangement of a stent 120 including diverter 121 that changes or alters the blood flow dynamics between the ICA 2 and the OA 4, preferably increasing the amount of blood entering the OA 4. FIG. 13 shows stent 110 positioned distal (e.g., downstream) of the OA 4, while FIG. 14 shows stent 120 positioned proximal (e.g., upstream) of the OA 4.

Figure 15:
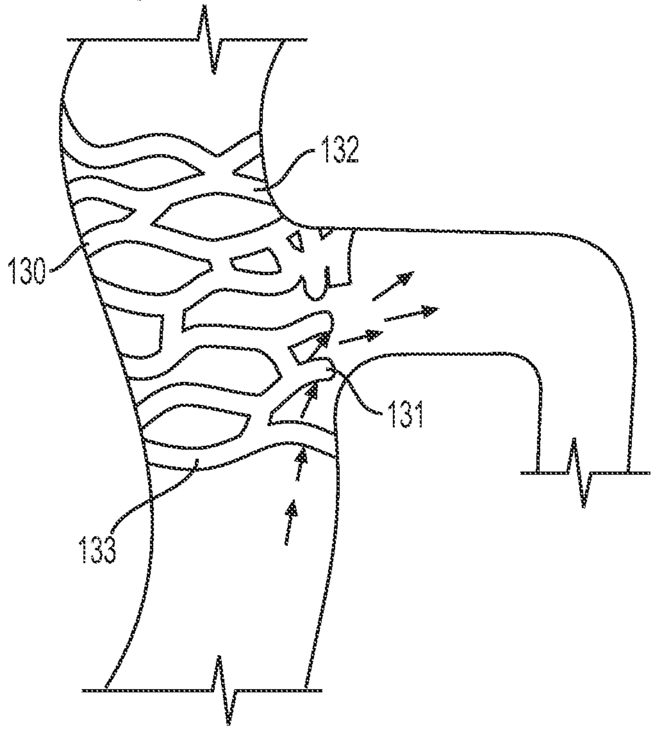

FIG. 15 illustrates a stent 130 that includes a diverter 131 that changes or alters the blood flow dynamics between the ICA 2 and the OA 4, preferably increasing the amount of blood entering the OA 4. Additionally, stent 130 includes both a distal (e.g., downstream) stent portion 132 and a proximal (e.g., upstream) stent portion 133. As shown, diverter 131 may extend from the proximal (e.g., upstream) stent portion 133 and toward the OA 4. Additionally, stent 130 includes a portion extending into the OA 4. The diverter 131 may be angled relative to the ICA 4 so as to direct blood flow impacting the diverter 131.

Figure 16:
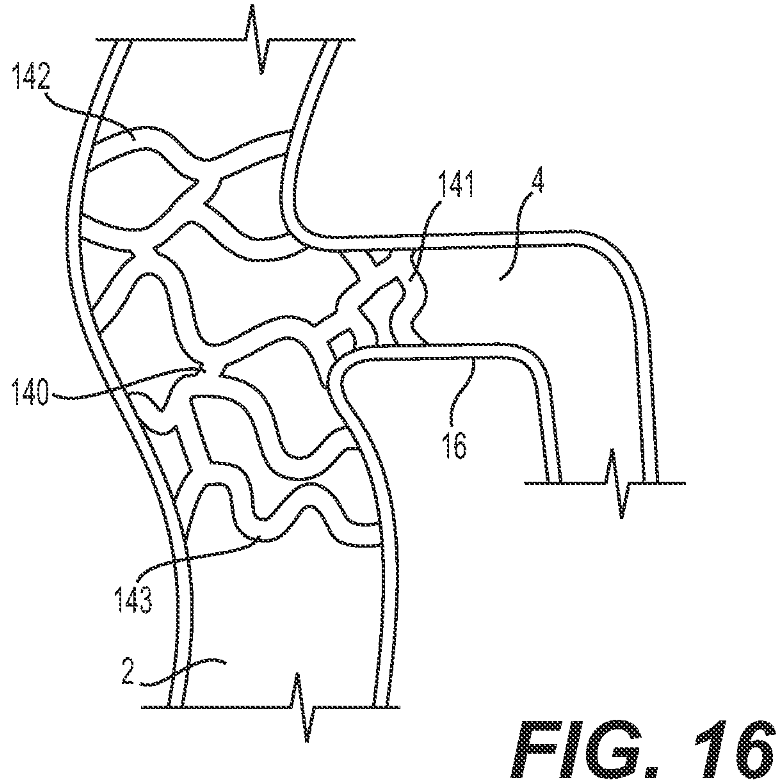

FIG. 16 shows a stent 140 configured for insertion within both the ICA 2 and the OA 4 and including a stent portion 141 that extends into the short limb 16 of the OA 4, a distal (e.g., downstream) stent portion 142 and a proximal (e.g., upstream) stent portion 143. As shown, a spacing between adjacent struts of stent portion 141 may be closer than a spacing between adjacent struts of either stent portion 142 and stent portion 143.

Figure 17:
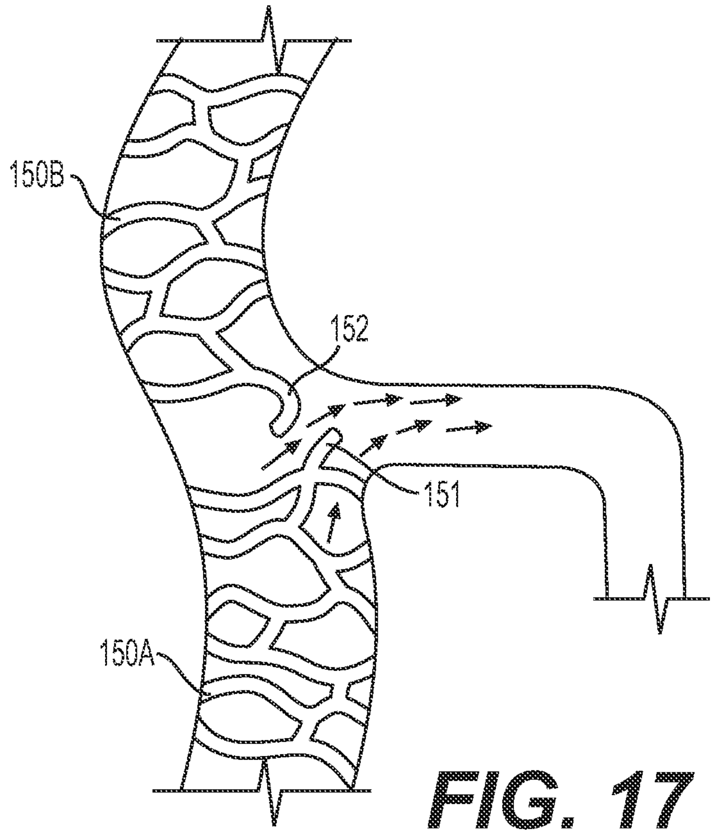

FIG. 17 illustrates an additional arrangement including a combination of multiple stents. For example, a first stent 150A is configured for insertion within the ICA 2 proximal (e.g., upstream) of the OA 4 and a second stent 150B is configured for insertion within the ICA 2 distal (e.g., downstream) of the OA 4. Stent 150A may further include a distal portion 151 comprising one or more flow diverter elements. Stent 150B may further include a proximal portion 152 comprising one or more flow diverter elements. As shown, each diverter of stent 150A and stent 150B may be angled so as to direct blood flow into OA 4. In some arrangements, each of the diverters of stent 150A and stent 150B may be generally parallel to one another.

Figure 18:
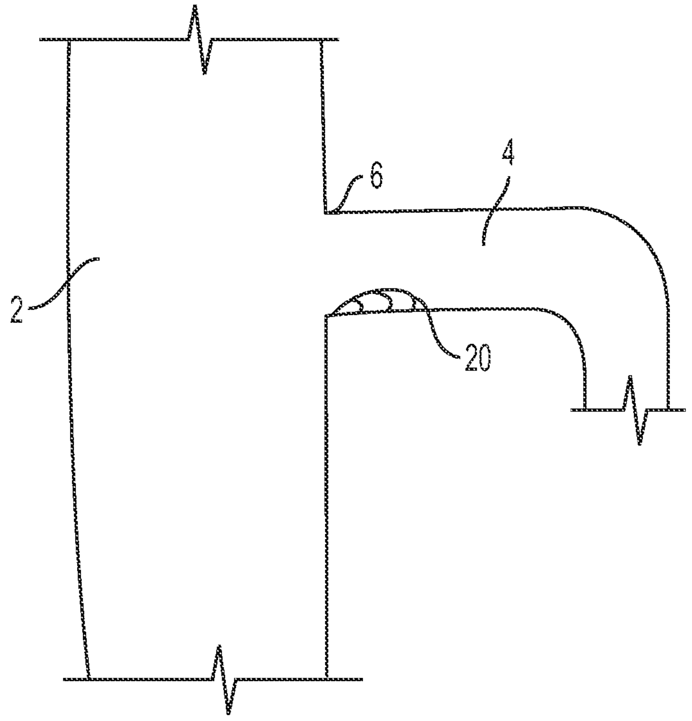
FIG. 18 illustrates a common location of an obstruction in the vasculature of the eye.

As noted above, any decrease in blood flow between the ICA 2 and the OA may be the result of one or more obstructions or constrictions within the vasculature. Thrombus, lesions, or other obstructions may be located in any of the ICA 2, the OA 4, the junction 6, or combinations thereof. FIG. 18 illustrates a common location of a thrombus or obstruction 20 in the OA 4.

Figure 19A:
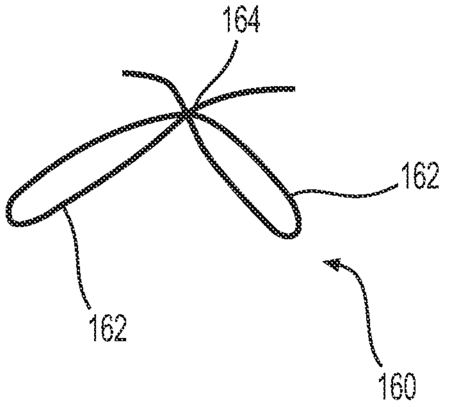
FIGS. 19A and 19B illustrate an arrangement of a self-expanding support member or ring according to the present disclosure.
Figure 19B:
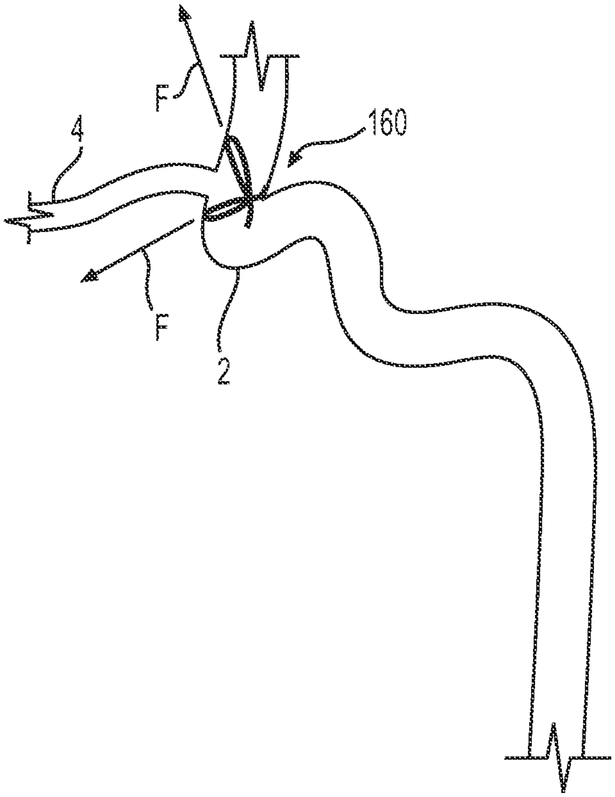
Figure 20A:
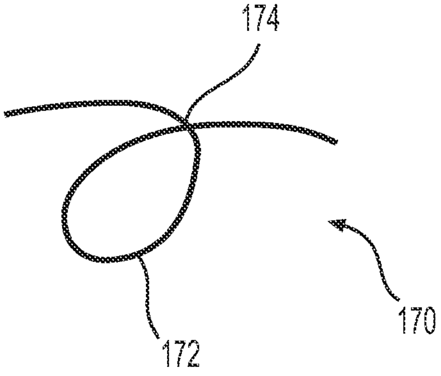
FIGS. 20A and 20B illustrate a further arrangement of a self-expanding support member or ring according to the present disclosure.
Figure 20B:
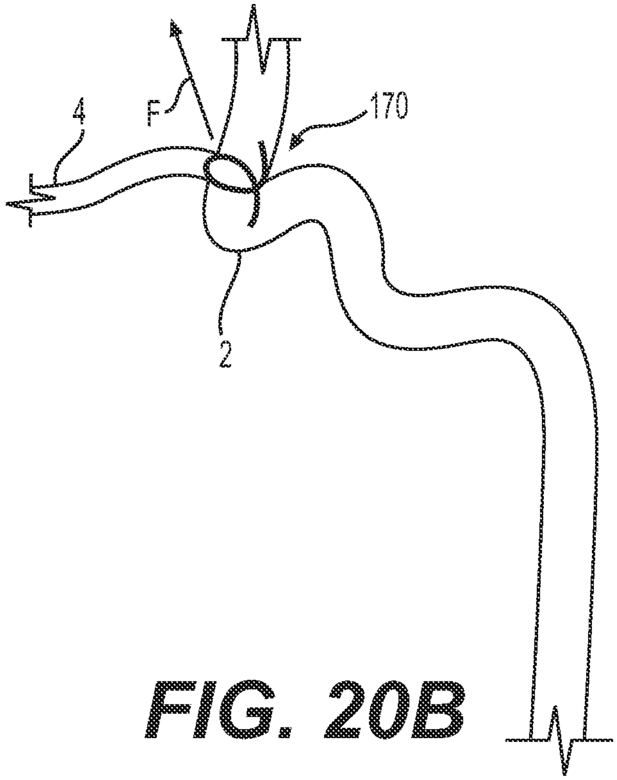

FIG. 19A illustrates an arrangement of a self-expanding support member or ring according to further arrangements. For example, as shown in FIG. 19A, a support ring 160 may include a pair of legs 162 extending from a base 164, each leg 162 being in the form of a loop. Free ends of ring 160 extend from base 164 opposite of legs 162. The legs 162 may be biased outwardly (e.g., away from) one another. In some examples, support ring 160 may comprise shape-memory alloy such as, for example, Nitinol. Support ring 160 may be delivered in a compressed configuration (not shown) via any appropriate device (e.g., a catheter or the like) to a location within one or both of ICA 2 and OA 4. Upon reaching the desired location, support ring 160 may be expelled from the delivery device (e.g., catheter) and allowed to expand, as shown in FIG. 19B. Upon expansion, legs 162 may apply an outward force F on opposite sides of OA 4 force the ostium between ICA 2 and OA 4 open. While support ring 160 is described as being a self-expandable, in other arrangements, support ring 160 may be expanded through via any appropriate method. Additionally, FIG. 20A illustrates a further arrangement of a self-expanding support member. For example, as shown in FIG. 20A, a support ring 170 may include a single (e.g., only one) leg 172. Similar to support ring 160, support ring 170 may be delivered in a compressed configuration (not shown) via any appropriate device (e.g., a catheter or the like) to a location within one or both of ICA 2 and OA 4. Upon reaching the desired location, support ring 170 may be expelled from the delivery device (e.g., catheter) and allowed to expand, as shown in FIG. 20B. Upon expansion, leg 172 may apply an outward force F on a side of OA 4 to force the ostium between ICA 2 and OA 4 open.

Figure 21:
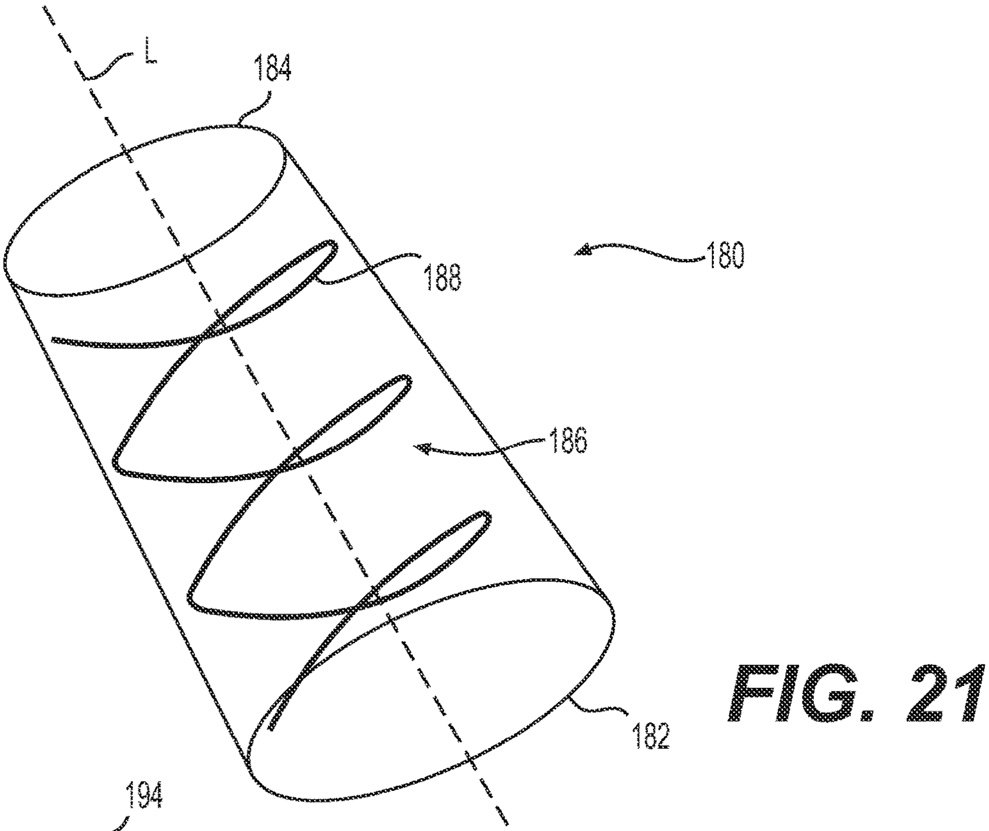
FIGS. 21-30 illustrate further exemplary arrangements of flow diverting structures according to the disclosure.

FIGS. 21-24 illustrate further exemplary arrangements of flow diverting structures according to the disclosure. For example, as shown in FIG. 21, a stent 180 may have a proximal end 182 and a distal end 184 and a length extending therebetween. As shown, stent 180 may have a tapered profile (e.g., proximal end 182 may have a first cross-sectional dimension while distal end 184 may have a second cross-sectional dimension different than the first cross-sectional dimension.) While not illustrated, stent 180 may include any number, arrangement, or shape of struts extending along the length. Additionally, although not shown, stent 180 may optionally include a covering, as described above. In the arrangement shown in FIG. 21, stent 180 may include a diverter in the form of a helical or partial helical element 186. As shown, element 186 may extend about or along an internal surface or diameter of stent 180, and may protrude inwardly from that internal stent surface. Element 186 may comprise a track or guide such that blood flow impacting element 186 or passing through stent 180 may be directed to flow along element 186 and/or toward OA 4 (FIG. 1). Element 186 may include one or more loops 188 extending along the length of stent 180. While three complete loops 188 are illustrated as equidistantly spaced along the length of stent 180 in FIG. 21, the disclosure is not so limited. Rather, any number of loops 188, equidistantly or not equidistantly, spaced along the length of stent 180 may be employed. Further, one or more features of element 186 may be adjusted as desired to achieve a desired flow of blood towards the OA 4. For example, the number of loops 186 per unit length (or pitch of helix), orientation of the element 186 (e.g., a left or right orientation of element 186), width of element 186 (e.g., a dimension of element 186 extending from a surface of stent 180 towards a central longitudinal axis L of stent 180), a height of element 186, a length of element 186 (e.g., element 186 may extend the entire length of stent 180 or less than the entire length of stent 180), and a number of elements 186 may be varied to achieve a desired effect on a flow of blood. For example, any one or more of the above-noted features of element 186 may be varied to achieve a venturi effect on a flow of blood passing through stent 180.

Figure 22:
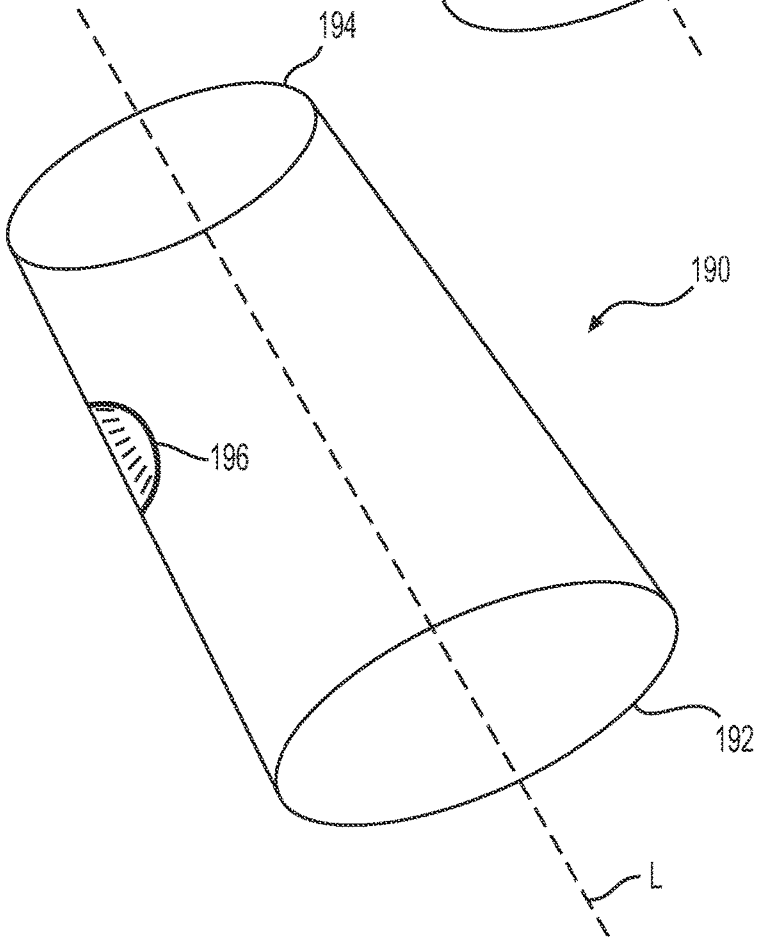

In a further arrangement, as shown in FIG. 22, a stent 190 may have a length extending between a proximal end 192 and a distal end 194. As shown, stent 190 may have a tapered profile (e.g., proximal end 192 may have a first cross-sectional dimension while distal end 194 may have a second cross-sectional dimension different than the first cross-sectional dimension.) While not illustrated, stent 190 may include any number, arrangement, or shape of struts extending along the length of stent 190. Additionally, although not shown, stent 180 may optionally include a covering, as described above. Rather than the inclusion of element 186, however, stent 190 may include a bump or projection 196. Projection 196 may extend radially inward from an internal circumferential wall toward a longitudinal axis L of stent 190. While only a single projection 196 is illustrated, in other arrangements, multiple projections 196 may extend from the internal circumferential wall of stent 190. Indeed, the number and arrangement of projections may be modified as desired so as to effect a flow of blood. For example, the number of projections 196 per unit length of stent 190, a dimension of a periphery of the projection 196 (e.g., a diameter), and/or a height of projection 196 extending from the circumferential wall of stent 190 toward longitudinal axis L. For example, any one or more of the above-noted features of projection 196 may be varied to achieve a venturi effect on a flow of blood passing through stent 190.

Figure 23:
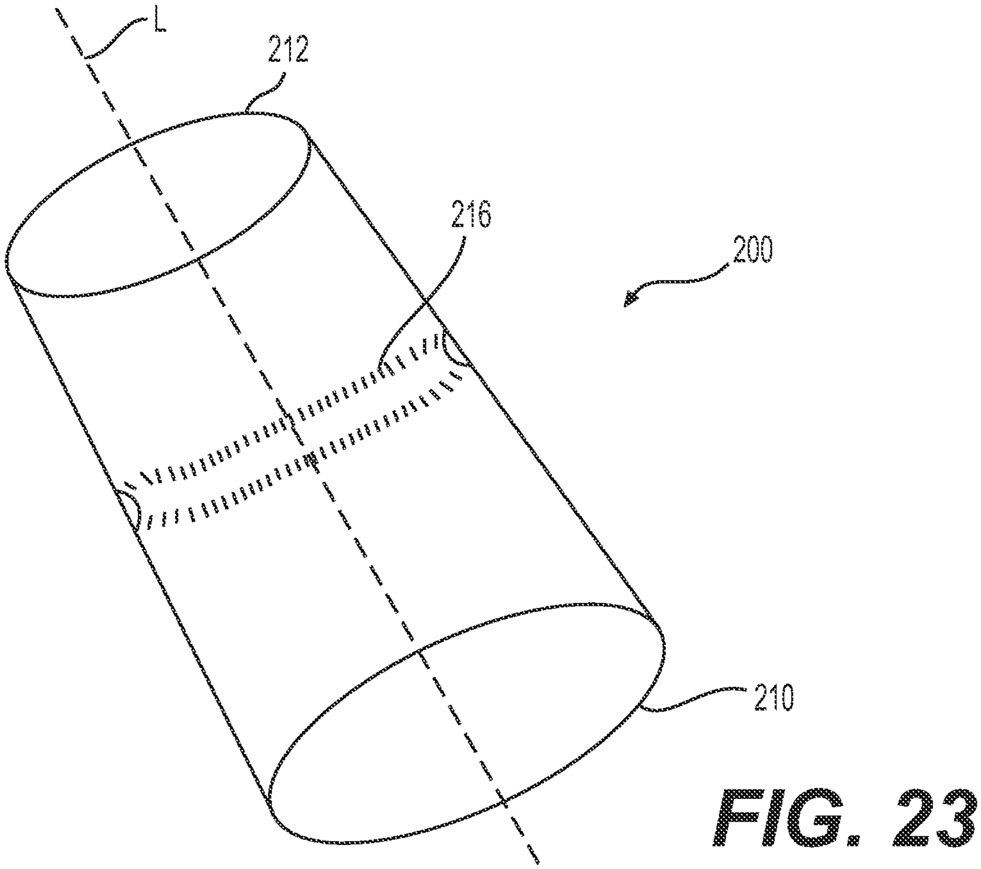

In a further arrangement, as shown in FIG. 23, a stent 200 may have a length extending between a proximal end 210 and a distal end 212. While not illustrated, stent 200 may include any number, arrangement, or shape of struts extending along the length of stent 200. Additionally, although not shown, stent 200 may optionally include a covering, as described above. Further, as shown in FIG. 23, stent 200 may include a raised annular ring or partial ring 216. Ring 216 may extend about at least a portion of an internal circumferential surface of stent 200 and protrude radially inwardly towards longitudinal axis L. While only a single ring 216 is illustrated, in other arrangements, multiple rings 216 may extend from the internal circumferential wall of stent 200. Indeed, the number and arrangement of rings 216 may be modified as desired so as to effect a flow of blood. For example, the number of rings (or partial rings) 216 per unit length of stent 200, a length of ring 216 (e.g., an arc length) extending about the circumferential surface of stent 200, a width of ring 216, and/or a height of ring 216 extending from the circumferential wall of stent 200 toward longitudinal axis L. For example, any one or more of the above-noted features of ring 216 may be varied to achieve a venturi effect on a flow of blood passing through stent 200.

Figure 24:
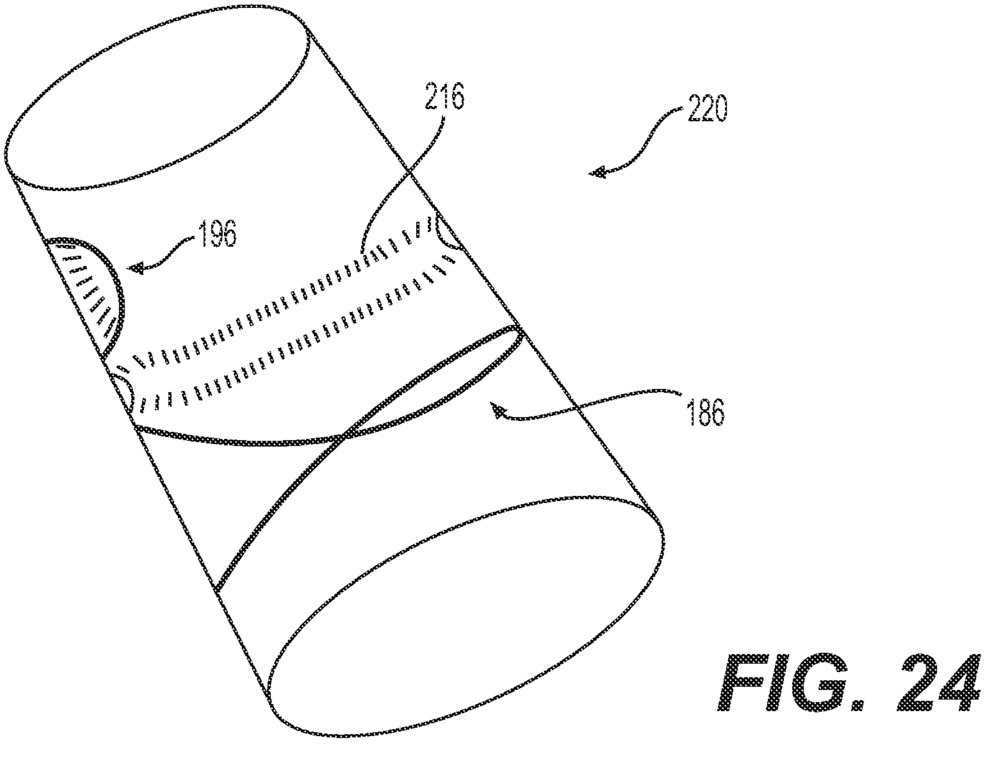

Additionally, as shown in FIG. 24, a stent 220 may include each of a helical element 186, a protrusion 196, and a ring 216. That is, as shown in FIG. 24, any of the blood flow diverting elements described in FIGS. 21-23 may be used in combination with one another so as to impart a desired effect on a flow of blood passing through stent 220. In such a manner, a flow of blood may be directed or guided toward OA 4.

Figure 25:
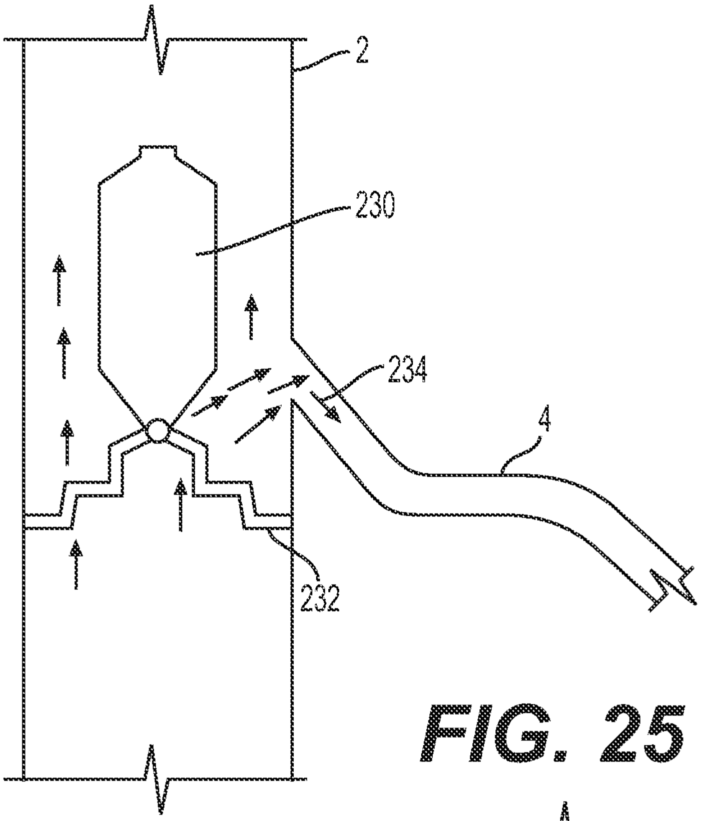
Figure 26:
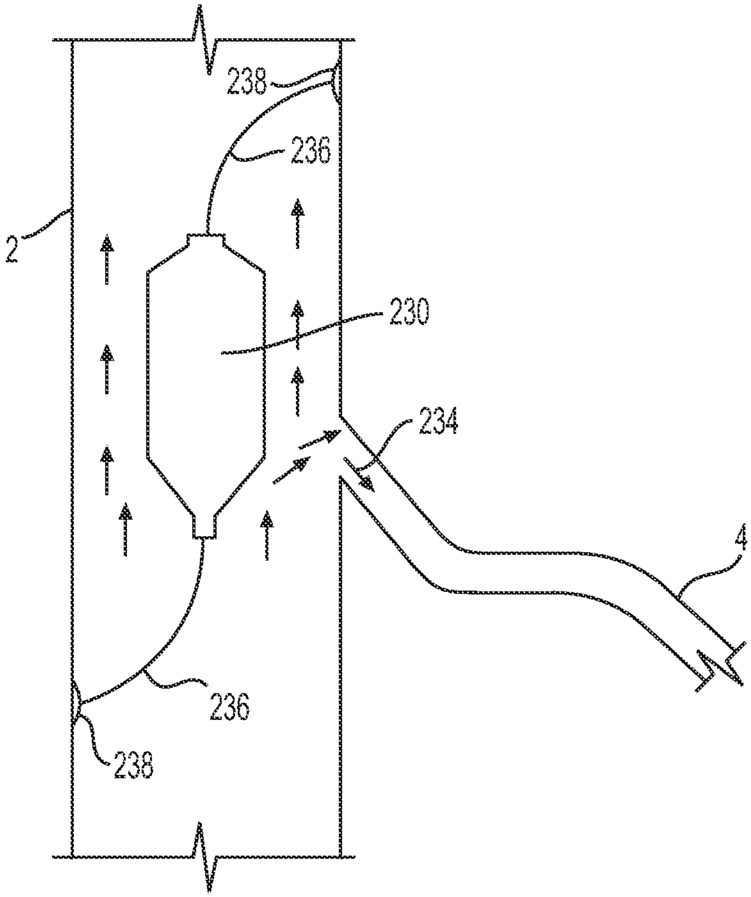

FIGS. 25 and 26 illustrate further exemplary arrangements of flow diverting structures according to the disclosure. As shown in FIG. 25, for example, a flow diverter 230 may be positioned within the ICA 2 so as to modify a flow of blood passing through the ICA 2. As shown, flow diverter 230 is supported via a mounting bracket or element 232. Mounting element 232 may be a bracket, frame, stent, ring or other such structure. For example, mounting element 232 may be an expandable (e.g., self-expandable Nitinol) ring such that upon positioning within the ICA 2, mounting element 232 may expand so as to contact walls of ICA 2, thus maintaining mounting element 232 in position relative to ICA 2. Alternatively, mounting element 232 may be secured to walls of the ICA 2 via any appropriate mechanism such as, for example, sutures, barbs, medical adhesives, or the like. While FIG. 25 illustrates mounting element 232 being constructed as a stepped or tapering structure, in other arrangements, mounting element 232 need not be stepped or tapered.

As shown in FIG. 25, mounting element 232 may be mounted within ICA 2 upstream of OA 4, and coupled to an upstream end of flow diverter 230. In other arrangements, mounting element 232 may be mounted within ICA 2 downstream of OA 4, and coupled to a downstream end of flow diverter 230. Still further, multiple mounting elements 232 (e.g., one coupled to an upstream end of flow diverter 230 and one coupled to a downstream end of flow diverter 230) may secure flow diverter 230 at a location within the ICA 2. In either arrangement, mounting element(s) 232 may enable a flow of blood to pass therethrough and around flow diverter 230. Flow diverter 230 may include a selectively inflatable balloon. In some arrangements, the balloon can be pre-inflated to a set size and positioned within ICA 2. Alternatively, the balloon can have an adjustable degree of inflation such that flow diverter 230 can dynamically modify a flow of blood passing through the ICA 2. Such a balloon may be inflated via an inflation lumen (e.g., a portion of a delivery catheter and/or a separate shaft, not shown). In some arrangements, the balloon may be filled with saline or a liquid polymer.

In any such arrangement, however, flow diverter 230 may modify a flow of blood passing through the vasculature. For example, flow diverter 230 may increase a velocity and alter a direction of the flow of blood. That is, the shape and/or size of flow diverter 230 may be selected so as to interfere with a flow of blood passing through ICA 2 by funneling, directing, or otherwise urging at least some of the flow of blood towards and/or into OA 4, as indicated by the arrows 234 in FIG. 25.

In an alternative arrangement, flow diverter 230 may be positioned within the ICA 2 via one or more arms 236. Arms 236 may include any one or more of string, suture material, or struts and may secure or mount flow diverter 230 within ICA 4. Each arm 236 may be secured to a wall of the ICA 4 via an anchor 238 including one or more of a suture, barb, adhesive or the like. In either arrangement, flow diverter 230 may adjust a velocity and/or direction of blood flow through ICA 2, as indicated by the arrows 234 in FIG. 26.

Figure 27:
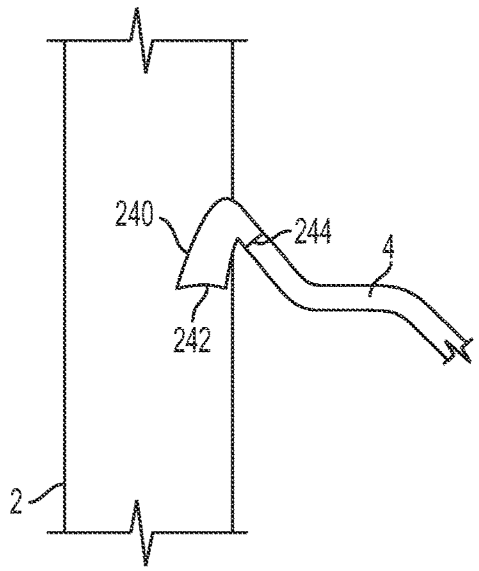

FIG. 27 illustrates a further arrangement of a flow diverter 240. Flow diverter 240 may be a funnel-shaped cylindrical member. Flow diverter 240 includes an upstream end 242 and a downstream end 244. As shown, upstream end 242 may have a dimension (e.g., diameter) larger than a dimension (e.g., diameter) of downstream end 244. Additionally, at least a portion of flow diverter 240 (e.g., upstream end 242) is positioned within ICA 2 while a further portion of flow diverter 240 (e.g., downstream end 244) is mounted within OA 4. As a flow of blood travels within the ICA 2 towards the OA, flow diverter 240 may funnel, guide, direct, or otherwise urge blood flow to enter OA 4. As shown, flow diverter 240 may include a bend between upstream end 242 and downstream end 244. Further, downstream end 244 may have a cross-sectional dimension configured for insertion within OA 4. For example, downstream end 244 may have a cross-sectional dimension (e.g., diameter) that is approximately the same as the cross-sectional dimension (e.g., diameter) of OA 4. Further, upstream end 242 may have a cross-sectional dimension (e.g., diameter) that is approximately the same as the cross-sectional dimension (e.g., diameter) of ICA 2. In some arrangements, flow diverter 240 may include an impermeable cover such that a flow of blood passing through flow diverter 240 does not pass through a side wall of flow diverter 240, but rather, is conveyed from upstream end 242 to downstream end 244.

Figure 28:
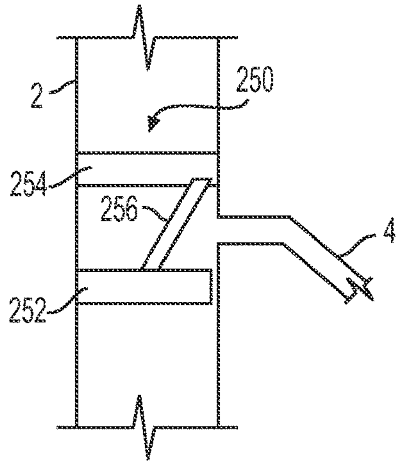

In a further arrangement, a flow diverter 250 may be mounted within the ICA 2, as shown in FIG. 28. Flow diverter 250 may include an upstream ring 252 (e.g., a ring positioned upstream of OA 4) and a downstream ring 254 (e.g., a ring positioned downstream of OA 4). In some arrangements, upstream ring 252 may be distinct and uncoupled from downstream ring 254. In other arrangements, upstream ring 252 may be coupled to downstream ring 254. Upstream ring 252 and downstream ring 254 may be formed of a self-expandable material such as, for example, Nitinol. A leaflet or valve 256 may be pivotably or otherwise moveably positioned between upstream ring 252 and downstream ring 254 (e.g., via a suture on one end of valve 256). That is, valve 256 may move so as to adjust an amount or velocity of blood entering OA 4. Valve 256 may move in accordance with systolic and diastolic pressure variations in a flow of blood. Movement of valve 256 may clean, wash, or otherwise prevent buildup of particulate on valve 256 as the flow of blood moves across a surface of valve 256. In an alternative arrangement, valve 256 may not be moveable. Rather, valve 256 may be secured so as to remain in place, thereby statically guiding, funneling, urging, or otherwise directing the flow of blood toward OA 4. Valve 256 may be comprised of any one or more of polyester, ePTFE, other polymers, and/or tissue. In a further arrangement, a plurality of valves 256 may be arranged to guide or direct the flow of blood toward the OA 4.

Figure 29:
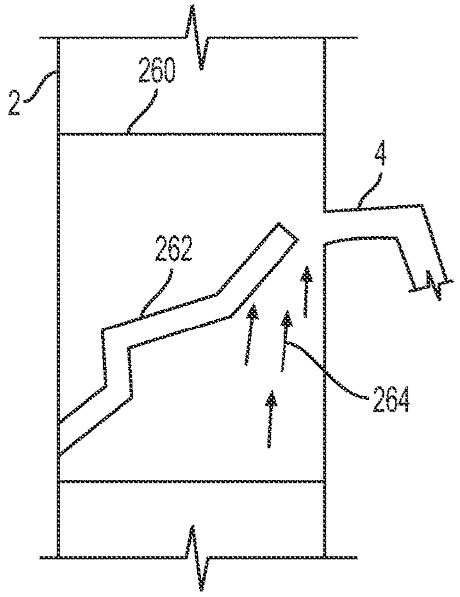

In a further arrangement, as shown in FIG. 29, a stent 260 may be positioned within the ICA 2. Additionally, stent 260 may include a strut or diverter arm 262. As shown in FIG. 29, diverter arm 262 may extend at an angle relative to a longitudinal axis of stent 260. Arm 262 may emanate from stent 260 at a position opposite the opening (e.g., ostium) to the OA 4, and extend in a downstream direction towards the side of ICA 2 closest to the OA 4. Arm 262 may have a free end near the ostium to the OA 4. Any of the angle, shape, thickness, and length of diverter arm 262 may be adjusted to modify an amount or velocity of blood entering OA 4. For example, diverter arm 262 may be angled so as to urge a flow of blood towards OA 4, as indicated by arrows 264 in FIG. 29. In some arrangements, diverter arm 262 may be coated or otherwise include a covering having one or more characteristics so as to modify a flow of blood. For example, in some arrangements, diverter arm 262 may be comprised of a bio-stable material such as ePTFE, thereby preventing a reaction between the flow of blood and diverter arm 262. In some arrangements, the entirety of stent 260, including diverter arm 262, may be coated, covered, or otherwise formed of ePTFE.

Figure 30:
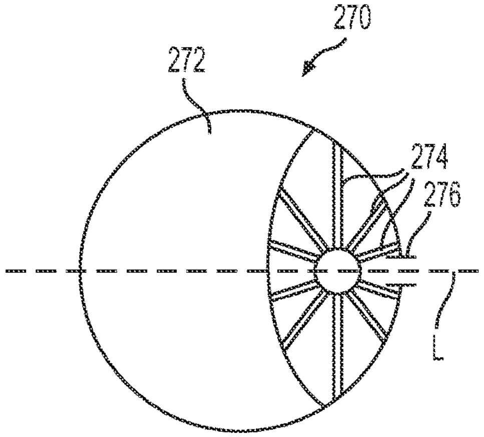

In a further arrangement, as shown in FIG. 30, a flow diverter 270 may include a covering 272 at least partially covering a plurality of spokes, struts, or fins 274. As shown, fins 274 may extend radially outwardly away from a longitudinal axis L of flow diverter 270. Fins 274 may have any shape and/or arrangement so as to focus or guide a flow of blood impacting fins 274 toward the OA 4. In addition, a number, an angle, a spacing, and/or a material of fins 274 may be adjusted so as to modify and/or guide the flow of blood toward the OA 4. For example, flow diverter 270 may include an opening 276 through which a flow of blood may be guided toward OA 4. As shown, opening 276 may extend through covering 272. In some arrangements, opening 276 may be received at least partially within OA 4.

Arrangements of the present disclosure may include percutaneous access and treatment of vascular structures at the rear of the eye, intended to provide devices and treatment methods for diseases of the eye related to compromised vascular flow. These methods include, but are not limited to, treatment for the symptoms related to Age Related Macular Degeneration, Glaucoma and Diabetic Retinopathy by placement of a stent in the ICA/OA ostium to provide treatment to stenosis in Ophthalmic/Internal Carotid Artery (ICA/OA) ostium, thereby restoring normal, near normal or improved blood flow to the rear of the eye, including the retina, choroid, and/or associated structures.

Another embodiment the present disclosure may include reducing and/or removing any blockage in the oxygen pathway to the eye. In this and other embodiments, reducing blockage(s) includes but is not limited to piercing or penetrating the blockage. In some arrangements, piercing and penetrating the blockage refers to obtaining sufficient blood and/or fluid flow through or around the blocked vascular area sufficient to provide a therapeutically beneficial amount of oxygen to the eye or a portion of the eye.

Another example of the present disclosure includes supplying oxygen to the eye or near the eye, wherein, in this embodiment, the source of the oxygen is external.

Another example of the present disclosure includes a medical device, such as a stent or the like, that may be used to open, clear, or improve vascular flow to or around the eye, wherein vascular flow mediates the amount of oxygen that is delivered to the eye.

The present disclosure relates generally to stents for use in body vessels to treat medical conditions. In particular, examples of the disclosure relate to novel asymmetric stents having opposing sets of curved apices, where the curved section of one set of apices has a radius of curvature that is greater than the curved section of the other set of apices, and may present a lower profile than conventional stents. The lower profile may present advantages for use in patients with particularly tortuous or small-diameter vessels.

In some embodiments, an asymmetric portion of a stent or a first asymmetric stent having a greater radius is configured for placement in the ICA 2. In other arrangements, an asymmetric portion of a stent or a second asymmetric stent having a smaller radius is configured for placement in the OA 4.

The asymmetric stent may be configured such that, when used with a graft, it will provide a sufficiently strong radial force at the graft's end openings to hold the graft material open against the vessel wall. Also, the stent is intended to be short in length (e.g., 0.5 mm, 1 mm, 2 mm in length) so that the graft will include flexibility sufficient to accommodate a patient's anatomy. This combination of flexibility and strong radial force provides an improved seal between the stent and artery wall. In addition, enhanced flexibility is provided as well, particularly when one or more stents are used to provide short segments and better accommodate curves.

For some of these embodiments, one or more layers of the implant device or stent may be configured to anchor or fix the implant device in a clinically beneficial position. For some embodiments, the implant device may be disposed in whole or in part within the vascular defect (e.g., obstruction, lesion, thrombus, vessel construction, etc.) in order to anchor or fix the device with respect to the vascular structure or defect. The one or more layers of the implant device may be configured to span an opening, neck or other portion of a vascular defect in order to isolate the vascular defect, or a portion thereof, from the patient's nominal vascular system in order to allow the defect to heal or to otherwise minimize the risk of the defect to the patient's health.

One or more stents according to the present disclosure may be manufactured from a super-elastic material. Solely by way of example, the super-elastic material may comprise a shape-memory alloy, such as a nickel titanium alloy (nitinol). If the stent comprises a self-expanding material such as nitinol, the stent may be heat-set into the desired expanded state, whereby the stent can assume a relaxed configuration in which it assumes the preconfigured first expanded inner diameter upon application of a certain cold or hot medium. Alternatively, the stent may be made from other metals and alloys that allow the stent to return to its original, expanded configuration upon deployment, without inducing a permanent strain on the material due to compression. Solely by way of example, the stent may comprise other materials such as stainless steel, cobalt-chrome alloys, amorphous metals, tantalum, platinum, gold and titanium. The stent also may be made from non-metallic materials, such as thermoplastics and other polymers.

The stent may be formed from a tube by laser cutting the pattern of cylindrical rings and undulating links in the tube. The stent also may be formed by laser cutting a flat metal sheet in the pattern of the cylindrical rings and links, and then rolling the pattern into the shape of the tubular stent and providing a longitudinal weld to form the stent.

The number and location of undulating links that interconnect adjacent cylindrical rings can be varied as the application requires. Since the undulating links typically do not expand when the cylindrical rings of the stent expand radially outwardly, the links are free to continue to provide flexibility and to also provide a scaffolding function to assist in holding open the artery. The addition or removal of the undulating links has very little impact on the overall longitudinal flexibility of the stent. Each undulating link is configured so that it promotes flexibility whereas some prior art connectors actually reduce flexibility of the stent.

Because of the undulating configuration of the links, the stent has a high degree of flexibility along the stent axis, which reduces the tendency of stent fishscaling. Stent fishscaling can occur when the stent is bent and portions of the stent project outward when the stent is in the unexpanded condition. The present disclosure includes undulating links so as to reduce the likelihood of fishscaling.

Further, because of the positioning of the links, and the fact that the links do not expand or stretch when the stent is radially expanded, the overall length of the stent is substantially the same in the unexpanded and expanded configurations. In other words, the stent will not substantially shorten upon expansion.

In operation, a wire guide may be advanced to the target site, and the cannula may be advanced over the wire guide to position the apparatus at the desired location in proximity to the target site, with the atraumatic tip reducing the likelihood of injury to bodily passageways during delivery. The outer sheath may be disposed over the cannula and the stent-graft during insertion to the target site. Upon proper positioning at the target site using a desired imaging modality, the outer sheath is then retracted to expose at least a portion of the stent.

When the stent is at least partially exposed, and it is desirable to deploy the proximal end of the stent, the cannula may be rotated in a clockwise direction until the longitudinal strut portions are aligned with the axial openings of the retaining member, e.g., in a reverse manner from which the longitudinal strut portions were loaded and secured to the retaining member. The proximal end of the stent then is allowed to self-expand due to the resilient nature of the struts, which will be inclined to move radially outward when no longer constrained by the outer wall portions. The remainder of the stent may be deployed by further retraction of the outer sheath or actuation of any other devices that are radially constraining the remainder of the stent.

Advantageously, the proximal end of the stent is radially restrained without the use of conventional trigger wires that span a full longitudinal length of the delivery system. Accordingly, the radial profile of the delivery system may be reduced without the provision of multiple trigger wires and one or more associated sleeves to house the trigger wires, thereby reducing packing density of the system. Moreover, deployment may be simplified as reduced deployment forces are expected to be needed relative to the use of conventional trigger wires.

Some embodiments of a delivery system for deployment of an implant device to treat a patient's vasculature include a microcatheter having an inner lumen extending the length thereof. The inner lumen provides a passageway for an implant device to treat a patient's vasculature. Some implant device embodiments may include one or more self-expanding resilient layers of thin coupled filaments, the layers defining a longitudinal axis between a proximal end and a distal end. Such embodiments can assume a radially-constrained, axially-elongated state configured for delivery through a microcatheter, with the thin woven filaments extending longitudinally from the proximal end to the distal end being radially adjacent to each other. The delivery system further includes an elongated delivery apparatus having a proximal end and a distal end releasably secured to a proximal portion (e.g., a hub or the like) of the implant device.

Access to a variety of blood vessels of a patient may be established, including arteries such as the femoral artery, the radial artery, cervical access, and the like, in order to achieve percutaneous access to a vascular defect. In general, the patient may be prepared for surgery, the access artery is exposed via a small surgical incision, and access to the lumen is gained using the Seldinger technique where an introducing needle is used to place a wire over which a dilator or series of dilators may dilate a vessel allowing an access sheath to be inserted into the vessel. This would allow the device to be used percutaneously. With an access sheath in place, a guiding catheter is used to provide a safe passageway from the entry site to a region near a treatment site. Exemplary guidewires for vascular use may include the Synchro2® made by Boston Scientific and the Glidewire Gold Neuro® made by MicroVention Terumo. Typical guidewire sizes may include 0.014 inches (0.36 mm) and 0.018 inches (0.46 mm). Once the distal end of the micro-catheter is positioned at the site, often by locating its distal end through the use of radiopaque marker material and fluoroscopy, the catheter is cleared. For example, if a guidewire has been used to position the microcatheter, it may be withdrawn from the microcatheter, and then the delivery apparatus may be advanced through the microcatheter.

Once the implant device is deployed at a desired treatment site, the microcatheter may then be withdrawn. Characteristics of the implant device and delivery apparatus discussed herein generally allow for retraction of the implant device after initial deployment into the vascular defect, but before detachment of the implant device. Therefore, it may also be possible and desirable to withdraw or retrieve an initially deployed implant device after the fit within the vascular defect has been evaluated in favor of a differently-sized implant device. The tip of a catheter, such as the microcatheter, may be advanced into or adjacent to the vascular site or vascular defect. An example of a suitable microcatheter having an inner lumen diameter of about 0.51 mm to about 0.56 mm is the Rapid Transit®. manufactured by Cordis Corporation. Examples of some suitable microcatheters may include microcatheters having an inner lumen diameter of about 0.66 mm to about 0.71 mm, such as the Rebar® by Ev3 Company, the Renegade Hi-Flow® by Boston Scientific Corporation, and the Mass Transit® by Cordis Corporation. Suitable microcatheters having an inner lumen diameter of about 0.79 mm to about 0.84 mm may include the Marksmen® by Chestnut Medical Technologies, Inc. and the Vasco 28® by Balt Extrusion. A suitable microcatheter having an inner lumen diameter of about 1.0 mm to about 1.04 mm includes the Vasco 35® by Balt Extrusion. These microcatheters are listed as exemplary embodiments only, and other suitable microcatheters may also be used with any of the embodiments discussed herein.

It is understood that the present disclosure is not be limited solely to changing vascular flow in order to improve or restore the amount of oxygen that is delivered to the eye. For example, in some arrangement, the vascular flow may be unaffected for the most part, but the amount or concentration of hemoglobin may be increased, thereby increasing the amount of oxygen that may be delivered to the eye. One skilled in the art may recognize that there are other biological systems or capabilities that may be used to increase the amount of oxygen that is delivered to the eye.

It is understood that any process, device, or agent that increases the availability of oxygen to the eye or eye region is included within the scope of the present disclosure. These processes, devices, and agents include, but are not limited to internal sources of oxygen, e.g., through the vascular system. These processes, devices, and agents include, but are not limited to external sources of oxygen, e.g., an injection into the eye or eye region with one or more substances that carries oxygen, a substance that captures or concentrates oxygen, a device that manufactures oxygen and/or one of more substances that result in an increase the amount of oxygen.

The present disclosure includes a system comprising one or more medical devices, (e.g., a stent) and an associated delivery apparatus; said system is used for increasing the amount of oxygenated blood in the eye area, or for increasing the amount of oxygen that is or can be delivered to the eye.

The disclosure further includes the use of one of more diagnostic devices or agents that allow a person to monitor oxygen content in the eye.

In another embodiment, a medical device or agent is capable of delivering drugs to the ostium for the purpose of improving vascular blood flow at the ostium and within the OA 4 . These drugs may include (but are not limited to) one or more of: a low dose PDE5 inhibitor (sildenafil), a VEGF-a inhibitor (ranibizumab/bevacizumab), a cytotoxic coating (Taxol/Rapamyacin), and/or a cytostatic coating (Sirolimus), other pharmaceuticals used to improve vascular blood flow, or combinations thereof.

In one embodiment, the ophthalmological disease or disorder treated or prevented by any of the methods or compositions described herein is age-related macular degeneration. Vision changes that can be associated with macular degeneration include distortions and/or blind spots (scotoma) detected using an Amsler grid, changes in dark adaptation (diagnostic of rod cell health), changes in color interpretation (diagnostic of cone cell health), and/or a decrease in visual acuity. Examples of age-related macular degeneration are normeovascular (also known as “dry”) and neovascular (also known as “wet” or “exudative”) macular degeneration.

In one embodiment, the dry age-related macular degeneration is associated with the formation of drusen. In one embodiment, treating or preventing dry macular degeneration encompasses treating or preventing an abnormality of the retinal pigment epithelium and/or underlying vasculature, known as choriocapilaries. Examples of abnormalities of the retinal pigment epithelium include geographic atrophy, non-geographic atrophy, focal hypopigmentation, and focal hyperpigmentation. In another embodiment, treating or preventing wet age-related macular degeneration encompasses treating or preventing choroidal neovascularization or pigment epithelial detachment.

In some embodiments, wet age-related macular degeneration is classified according to the appearance of its choroidal neovascularization (CNV), into classic, occult or mixed (classic and occult) CNV types, as determined by an angiography, known as fluorescence angiography. Classic, occult or mixed (classic and occult) CNV classification can be based on the time, intensity and level of definition of dye appearance, and leakage from the CNV, as assessed by the fluorescein angiography. In some embodiments, the subject has classic CNV (e.g., pure classic) or mixed CNV (predominantly or minimally classic CNV). In some embodiments, the subject has occult CNV (e.g., pure occult CNV).

In certain embodiments, the ophthalmological disease or disorder is a cataract (e.g., age-related cataract), diabetic macula edema, macular telangiectasia (e.g., type 1 or 2 macular telangiectasia), anterior ischemic optic neuropathy (AION) (either arteritic or non-arteritic), amaurosis fugax, atrophic macular degeneration, chorioretinopathy (e.g., central serous chorioretinopathy), retinal inflammatory vasculopathy, pathological retinal angiogenesis, age-related maculopathy, retinoblastoma, Pseudoxanthoma elasticum, a vitreoretinal disease, choroidal sub-retinal neovascularization, central serous chorioretinopathy, ischemic retinopathy, hypertensive retinopathy or diabetic retinopathy (e.g., non-proliferative or proliferative diabetic retinopathy, such as macular edema or macular ischemia), retinopathy of prematurity (e.g., associated with abnormal growth of blood vessels in the vascular bed supporting the developing retina), venous occlusive disease (e.g., a retinal vein occlusion, branch retinal vein occlusion or central retinal vein occlusion), arterial occlusive disease (e.g., branch retinal artery occlusion (BRAO), central retinal artery occlusion or ocular ischemic syndrome), central serous chorioretinopathy (CSC), cystoid macular edema (CME) (e.g., affecting the central retina or macula, or after cataract surgery), retinal telangiectasia (e.g., characterized by dilation and tortuosity of retinal vessels and formation of multiple aneurysms, idiopathic JXT, Leber's miliary aneurysms, or Coats' disease), arterial macroaneurysm, retinal angiomatosis, radiation-induced retinopathy (RI RP), or rubeosis iridis (e.g., associated with the formation of neovascular glaucoma, diabetic retinopathy, central retinal vein occlusion, ocular ischemic syndrome, or chronic retinal detachment).

We claim:

1. A method of treating an eye of a patient, the method including:

positioning an expandable strut structure within an internal carotid artery, near an ostium at a junction between the internal carotid artery and an ophthalmic artery, using a delivery device, wherein the expandable strut structure includes two legs, the two legs including a first leg and a second leg; and expelling, from the delivery device, a support member of the expandable strut structure, thereby expanding the two legs of the expandable strut structure to contact portions of the internal carotid artery adjacent to the ostium, with the first leg applying a first outward force to the ostium, in a first direction, and the second leg applying a second outward force to the ostium, in a second direction that is different from and non- parallel to the first direction, the first outward force and the second outward force being applied on opposite sides of the ostium, thereby opening the ostium and directing blood flow towards the ophthalmic artery.

2. The method of claim 1, wherein the support member is self-expanding.

3. The method of claim 1, wherein the support member is a support ring.

4. The method of claim 3, wherein the support ring is formed of a shape memory alloy.

5. The method of claim 4, wherein the shape memory alloy is Nitinol.

6. The method of claim 1, wherein each of the two legs is in the form of a loop.

7. The method of claim 1, wherein the positioning the expandable strut structure includes positioning the expandable strut structure such that, upon expansion of the expandable strut structure, the first leg is positioned within the internal carotid artery upstream of the ophthalmic artery, and the second leg is positioned within the internal carotid artery downstream of the ophthalmic artery.

8. The method of claim 1, wherein the directing blood flow results in an increase in oxygen delivery to the eye of the patient.

9. A method of treating an eye of a patient, comprising:

positioning an expandable strut structure within an internal carotid artery, near an ostium at a junction between the internal carotid artery and an ophthalmic artery, using a delivery device, wherein the expandable strut structure has a single leg that is in the form of a loop; and expelling, from the delivery device, a support member of the expandable strut structure, thereby expanding the single leg of the expandable strut structure to contact a portion of the ostium, and at least a portion of the single leg to be positioned within the ostium, with the single leg applying a radially outward force on one side of the ostium, thereby opening the ostium and directing blood flow towards the ophthalmic artery.

10. The method of claim 9, wherein the support member is self-expanding.

11. The method of claim 9, wherein the support member is a support ring.

12. The method of claim 11, wherein the support ring is formed of a shape memory alloy.

13. The method of claim 12, wherein the shape memory alloy is Nitinol.

14. The method of claim 9, wherein the directing blood flow results in an increase in oxygen delivery to the eye of the patient.

15. A method of treating an eye of a patient, the method including:

positioning a self-expanding support member within an internal carotid artery, near an ostium at a junction between the internal carotid artery and an ophthalmic artery, using a delivery device, wherein the support member includes two legs in the form of loops, including a first leg and a second leg, and wherein the support member is formed of a shape memory alloy; and expelling, from the delivery device, the support member, such that the support member expands and the first leg applies a first outward force to the ostium by contacting a portion of the internal carotid artery near the ostium, in a first direction, and the second leg applies a second outward force to the ostium by contacting another portion of the internal carotid artery near the ostium, in a second direction that is different from and non-parallel to the first direction, the first outward force and the second outward force being applied on opposite sides of the ostium, thereby opening the ostium and directing blood flow towards the ophthalmic artery.

16. The method of claim 15, wherein the support member is a support ring.

17. The method of claim 15, wherein the shape memory alloy is Nitinol.

18. The method of claim 15, wherein positioning the support member includes positioning the support member such that, upon expansion of the support member, the first leg is positioned within the internal carotid artery upstream of the ophthalmic artery, and the second leg is positioned within the internal carotid artery downstream of the ophthalmic artery.

* * * * *